United States Patent
Li et al.

(10) Patent No.: US 10,629,064 B2
(45) Date of Patent: *Apr. 21, 2020

(54) CONSUMABLE CRYOPRESERVED CELLS TRANSIENTLY OVEREXPRESSING GENE(S) ENCODING DRUG TRANSPORTER PROTEIN(S) AND/OR DRUG METABOLIZING ENZYME(S)

(71) Applicant: Corning Incorporated, Corning, NY (US)

(72) Inventors: Na Li, Winchester, MA (US); Jie Wang, Winchester, MA (US); Christopher J. Patten, Scituate, MA (US)

(73) Assignee: Corning Incorporated, Corning, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/407,860

(22) Filed: May 9, 2019

(65) Prior Publication Data

US 2019/0263884 A1 Aug. 29, 2019

Related U.S. Application Data

(60) Continuation of application No. 15/988,819, filed on May 24, 2018, now Pat. No. 10,336,806, which is a continuation of application No. 15/688,983, filed on Aug. 29, 2017, now Pat. No. 10,047,136, which is a continuation of application No. 14/972,012, filed on Dec. 16, 2015, now Pat. No. 9,822,160, which is a division of application No. 14/644,000, filed on Mar. 10, 2015, now abandoned, which is a continuation of application No. PCT/US2013/059152, filed on Sep. 11, 2013.

(60) Provisional application No. 61/699,466, filed on Sep. 11, 2012.

(51) Int. Cl.

| C12N 5/071 | (2010.01) |
|---|---|
| C12N 5/00 | (2006.01) |
| C12N 5/02 | (2006.01) |
| G08B 29/18 | (2006.01) |
| G08B 13/00 | (2006.01) |
| G08B 25/00 | (2006.01) |
| G08B 13/196 | (2006.01) |
| G08B 25/08 | (2006.01) |
| G05B 15/02 | (2006.01) |
| A01N 1/02 | (2006.01) |
| C07K 14/705 | (2006.01) |
| C12N 15/85 | (2006.01) |
| G01N 33/50 | (2006.01) |

(52) U.S. Cl.
CPC .......... *G08B 29/185* (2013.01); *A01N 1/021* (2013.01); *A01N 1/0284* (2013.01); *C07K 14/705* (2013.01); *C12N 5/00* (2013.01); *C12N 5/067* (2013.01); *C12N 5/069* (2013.01); *C12N 15/85* (2013.01); *G01N 33/5008* (2013.01); *G05B 15/02* (2013.01); *G08B 13/00* (2013.01); *G08B 13/196* (2013.01); *G08B 25/001* (2013.01); *G08B 25/08* (2013.01); *C12N 2510/00* (2013.01); *G01N 2333/705* (2013.01); *G05B 2219/2642* (2013.01)

(58) Field of Classification Search
CPC .............................. C07K 14/705; C12N 15/85
See application file for complete search history.

(56) References Cited

U.S. PATENT DOCUMENTS

| 5,166,059 A | 11/1992 | Pastan et al. |
|---|---|---|
| 5,849,525 A | 12/1998 | Hediger |
| 5,849,998 A | 12/1998 | Gottesman et al. |
| 5,851,819 A | 12/1998 | Gottesman et al. |
| 5,928,637 A | 7/1999 | Gottesman et al. |
| 5,972,702 A | 10/1999 | Beier et al. |
| 6,025,160 A | 2/2000 | Brun et al. |
| 6,063,623 A | 5/2000 | Koepsell et al. |
| 6,063,634 A | 5/2000 | Chomka et al. |
| 6,200,959 B1 | 3/2001 | Haynes et al. |
| 6,262,333 B1 | 7/2001 | Endege et al. |
| 6,262,334 B1 | 7/2001 | Endege et al. |
| 6,313,277 B1 | 11/2001 | Ross et al. |
| 6,432,631 B1 | 8/2002 | Cihlar |
| 6,440,730 B1 | 8/2002 | Von Laer et al. |
| 6,485,933 B1 | 11/2002 | Bandman et al. |

(Continued)

FOREIGN PATENT DOCUMENTS

| EP | 420911 B1 | 9/1996 |
|---|---|---|
| EP | 1223217 A1 | 7/2002 |

(Continued)

OTHER PUBLICATIONS

Mueller (2011, Antimicrob Agents Chemother, 55:3091-3098).*

(Continued)

*Primary Examiner* — Valarie E Bertoglio
(74) *Attorney, Agent, or Firm* — Annie J. Kock; Rich-Henry Schabowsky

(57) ABSTRACT

The present invention discloses cryopreserved recombinant cells for screening drug candidates that transiently overexpress one or more drug transporter proteins and/or drug metabolizing enzymes. Advantageously, such cells provide a cost-efficient consumable product that streamlines the process of screening whether drug candidates are substrates or inhibitors of drug transporter proteins and/or drug metabolizing enzymes.

8 Claims, 28 Drawing Sheets

(56) References Cited

U.S. PATENT DOCUMENTS

| | | |
|---|---|---|
| 6,589,763 B1 | 7/2003 | Von Laer et al. |
| 6,640,730 B2 | 11/2003 | Tsai |
| 6,680,379 B1 | 1/2004 | Sun |
| 6,692,934 B1 | 2/2004 | Kirchgessner et al. |
| 6,753,177 B1 | 6/2004 | Stocker et al. |
| 6,812,339 B1 | 11/2004 | Venter et al. |
| 6,908,748 B2 | 6/2005 | Ota et al. |
| 6,986,997 B1 | 1/2006 | Endou et al. |
| 7,045,316 B2 | 5/2006 | Nezu et al. |
| 7,071,305 B2 | 7/2006 | Cihlar |
| 7,105,315 B2 | 9/2006 | Lasek et al. |
| 7,229,825 B2 | 6/2007 | Cui et al. |
| 7,235,375 B2 | 6/2007 | Kirchgessner et al. |
| 7,415,358 B2 | 8/2008 | Mendrick et al. |
| 7,507,546 B2 | 3/2009 | Zerangue et al. |
| 7,589,186 B2 | 9/2009 | Cihlar |
| 7,590,493 B2 | 9/2009 | Mendrick et al. |
| 7,601,494 B2 | 10/2009 | Tian et al. |
| 7,700,095 B2 | 4/2010 | Xu et al. |
| 7,745,391 B2 | 6/2010 | Mintz et al. |
| 7,776,588 B2 | 8/2010 | Mealey |
| 7,795,392 B2 | 9/2010 | Kirchgessner et al. |
| 7,892,728 B2 | 2/2011 | Moriyama et al. |
| 8,278,032 B2 | 10/2012 | Moriyama et al. |
| 8,338,124 B2 | 12/2012 | Van Rompaey et al. |
| 8,748,128 B2 | 6/2014 | Nezu et al. |
| 2003/0087391 A1 | 5/2003 | Bandman et al. |
| 2005/0170392 A1 | 8/2005 | Zerangue |
| 2006/0014940 A1 | 1/2006 | Mount et al. |
| 2007/0037165 A1 | 2/2007 | Venter et al. |

FOREIGN PATENT DOCUMENTS

| | | |
|---|---|---|
| EP | 1114830 B1 | 12/2006 |
| EP | 2030985 A1 | 3/2009 |
| EP | 1486510 B1 | 5/2009 |
| EP | 1183270 B1 | 5/2010 |
| EP | 2316848 A1 | 5/2011 |
| JP | 51037132 A | 3/1976 |
| WO | 8912109 A1 | 12/1989 |
| WO | 9850546 A2 | 11/1998 |
| WO | 0071566 A2 | 11/2000 |
| WO | 03072759 A2 | 9/2003 |
| WO | 2014043170 A1 | 3/2014 |

OTHER PUBLICATIONS

Terada (2006, Pharmacological Research 23:1696-1701).*

English Translation of JP2018103511 Office Action dated Jul. 10, 2019; 3 Pages; Japanese Patent Office.

Abe, et al., "Identification of a Novel Gene Family Encoding Human Liver-specific Organic Anion Transporter LST-1*", The Journal of Biological Chemistry, Jun. 11, 1999, vol. 274, No. 24, pp. 17159-17163, USA.

Bahn et al. "Interaction of the metal Chelator 2,3-Dimercapto-1-propanesulfonate with the rabbit multispecific organic anion transporter 1 (rbOAT1)" Molecular Pharmacology, 62(5) 2002, pp. 1128-1136.

Brady, "Creating Cell-Based Assays for Screening GPCRs, Ion Channels and Other Targets in Cell Lines and Primary Cells Using the MaxCyte STX(TM) Scalable Transient Transfection System" MaxCyte, 2015, p. 1, http://www.maxcyte.com/resources/Posters-Presentations/Brady_SBS_2010_Poster_Final.pdf.

Brimer et al. "Creation of Polarized Cells Coexpressing CYP3A4, NADPH Cytochrome P450 Reductase and MDR1/P-glycoprotein" Pharmaceutical Research, vol. 17, No. 7, 2000.

Brouwer, et al., "In Vitro Methods to Support Transporter Evaluation in Drug Discovery and Development, American Society for Clinical Pharmacology and Therapeutics", Apr. 10, 2013, USA.

Chen et al., "Application of large-scale transient transfection to cell-based functional assays for ion channels and GPCRs", Methods in Enzymology, vol. 485, No. C, 2010, pp. 293-309.

Donohue, "Recombinant Hep G2 cells that express alcohol dehydrogenase and cytochrome P450 2E1 as a model of ethanol-elicited cytotoxicity", The International Journal of Biochemistry and Cell Biology, 2006, 38:92-101.

Hillgreen et al "Emerging Transporters of Clinical Importance: An Update From the International Transporter Consortium", Clinical Pharmacology and Therapeutics, 12 pgs.

Giacomini et al. "Membrane transporters in drug development", vol. 9 2010, pp. 215-236.

Hirano, et al., "Contribution of OATP2 (OATP1B1) and OATP8 (OATP1B3) to the Hepatic Uptake of Pitavastatin in Humans", The Journal of Pharmacology and Experimental Therapeutics, The American Society for Pharmacology and Experimental Therapeutics, May 24, 2004, vol. 311, No. 1, pp. 139-146, USA.

Hoog "Mammalian alcohol dehydrogenase Functional and structural implications" J Biomed Sci, 2001, 8:71-76.

Hsiang, et al., "A Novel Human Hepatic Organic Anion Transporting Polypeptide (OATP2)", The Journal of Biological Chemistry, Dec. 24, 1999, vol. 274, No. 52, pp. 37161-37168, USA.

JP2015531332 Office Action dated May 9, 2017, Japan Patent Office.

Kitamura, et al., "Involvement of Multiple Transporters in the Hepatobiliary Transport of Rosuvastatin, Drug Metabolism and Disposition", The American Society for Pharmacology and Experimental Therapeutics, Jul. 7, 2008, vol. 36, No. 10, pp. 2014-2023, USA.

Lanzrein, Markus, International Search Report in PCT/US2013/059152, dated Dec. 10, 2013.

Lau, "Effect of OATP1B Transporter Inhibition on the Pharmacokinetics of Atorvastatin in Healthy Volunteers", Clinical Pharmacology and Therapeutics, 2007, 81: 195-204.

Li et al., "Characterization of ABC transporters and SLC transporters in sandwich cultured human cryopreserved hepatocytes", Drug Metabolism Reviews, Nov. 2011, vol. 43, Suppl. 2, Sp. Iss. S1, Nov. 2011, p. 192.

Masuda, Journal of the American Society of Nephrology, 17 (2006) pp. 2127-2135.

Maurisse et al., "Comparitive transfection of DNA into primary and transformed mammalian cells from different lineages", BMC Biotechnology, 2010, 10:9, pp. 1-9.

Monks et al., "Potent cytotoxicity of the phosphatase inhibitor microcystin LR and microcystin analogues in OATP1B1- and OATP1B3-expressing HeLa cells", Molecular Cancer Therapeutics, Feb. 2007, vol. 6, No. 2, pp. 587-598.

Nakamura, Yukari, International Preliminary Report on Patentability in PCT/US2013/059152, dated Mar. 17, 2015.

Nozawa, "Functional Characterization of pH-sensitive Organic Anion Transporting Polypeptide OATP-B in Human", 2004, Journal of Pharmacology and Experimental Therapeutics, 308: 438-445.

P. Sharma, et al., "Validation of cell-based OATP1B1 assays to assess drug transport and the potential for drug-drug interaction to support regulatory submissions", Informa Healthcare, Xenobiotica, 2010, vol. 40, No. 1, pp. 24-37, http://www.infomahealthcare.com/xen, UK.

Shield "Human Catechol O-Methyltransferase genetic variation: gene resequencing and functional chartacterization of variant allozymes", (2004, Molecular Psychiatry, 9:151-160.

Soars, et al., "The Development, Characterization, and Application of an OATP1B Inhibition Assay in Drug Discovery", Drug Metabolism and Disposition, The American Society for Pharmacology and Experimental Therapeutics,May 14, 2012, vol. 40, No. 8, pp. 1641-1648, USA.

Strassburg et al. "Polymorphic Gene Regulation and Interindividual Variation of UDP-glucuronosyltransferase Activity in Human Small Intestine", The Journal of Biological Chem., vol. 275 No. 46 (2000) pp. 36164-36171.

Strassburg et al. "UDP-glucuronosyltransferase Activity in human liver and colon", Gastroenterology 1999; 116: pp. 149-160.

Sun, "Characterization of tamoxifen and 4-hydroxytamoxifen glucuronidation by human UGT1A4 variants", 2006, Breast Cancer Research, 8(4):1-11.

(56) References Cited

OTHER PUBLICATIONS

Tamai et al., 2001, "Functional Characterization of Human Organic Anion Transporting Polypeptide B (OATP-B) in Comparison with Liver-Specific OATP-C", Pharmaceutical Research, 18: 1262-1269.

Taub et al. "Digoxin is not a substrate for organic anion-transporting polypeptide transporters", published online Aug. 2011, Drug Metabolism and Disposition, 39: 2093-2102.

Terao Use of electroporation to introduce biologically (2000, Journal Biological Chemistry, 275:20690-30700).

U.S. Department of Health and Human Services, FDA "Guidance for Industry:Drug Interaction Studies Study Design, Data Analysis, Implications for Dosing, and Labeling Recommendations" Clinical Pharmacology, Feb. 2012. 79 pgs.

Wright et al., "Rapid screening of human OATP1B1 and OATP1B3 mediated drug interactions in stably transfected human embryonic kidney HEK-293 cell lines using flow cytometry and fluorescence microplate methods", Drug Metabolism Reviews, vol. 43, Suppl. 2, Sp. Iss. S1, Nov. 2011, pp. 208-209.

Yamashiro, et al., "Involvement of Transporters in the Hepatic Uptake and Biliary Excretion of Valsartan, a Selective Antagonist of the Angiotensin II AT1-Receptor, in Humans", Drug Metabolism and Disposition, The American Society for Pharmacology and Experimental Therapeutics, Apr. 18, 2006, vol. 34, No. 7, pp. 1247-1254, USA.

Zaman et al., "Cryopreserved cells facilitate cell-based drug discovery", Drug Discovery Today, Jul. 19, 2007, vol. 12, No. 13-14, pp. 521-526.

Zhu, "Use of Cryopreserved Transiently Transfected Cells in high-throughput Pregnane X Receptor Transactivation Assay", J Biomol Screen, 2007, 12: 248-254.

Chinese Office Action CN201380057012.1 dated May 25, 2016.

EP13774270.6 Office Action dated Nov. 27, 2017, European Patent Office.

Lankisch, 2005, Molecular Pharmacology, 67: 1732-1739.

Tur-Kaspa, 1986, Mol. Cell. Biol., 6:716-718.

Iwai (2010, Pharmacogenetics, 14: 749-757).

Fraser et al. "The role of the SCF/KIT signalling pathway in embryonic stem cells" 2010, The University of Edinburgh, phD Thesis, 254 Pgs.

Korean Patent Application No. 20157008921; English Translation of the Office Action dated Aug. 25, 2019; Korea Patent Office; 3 Pgs.

* cited by examiner

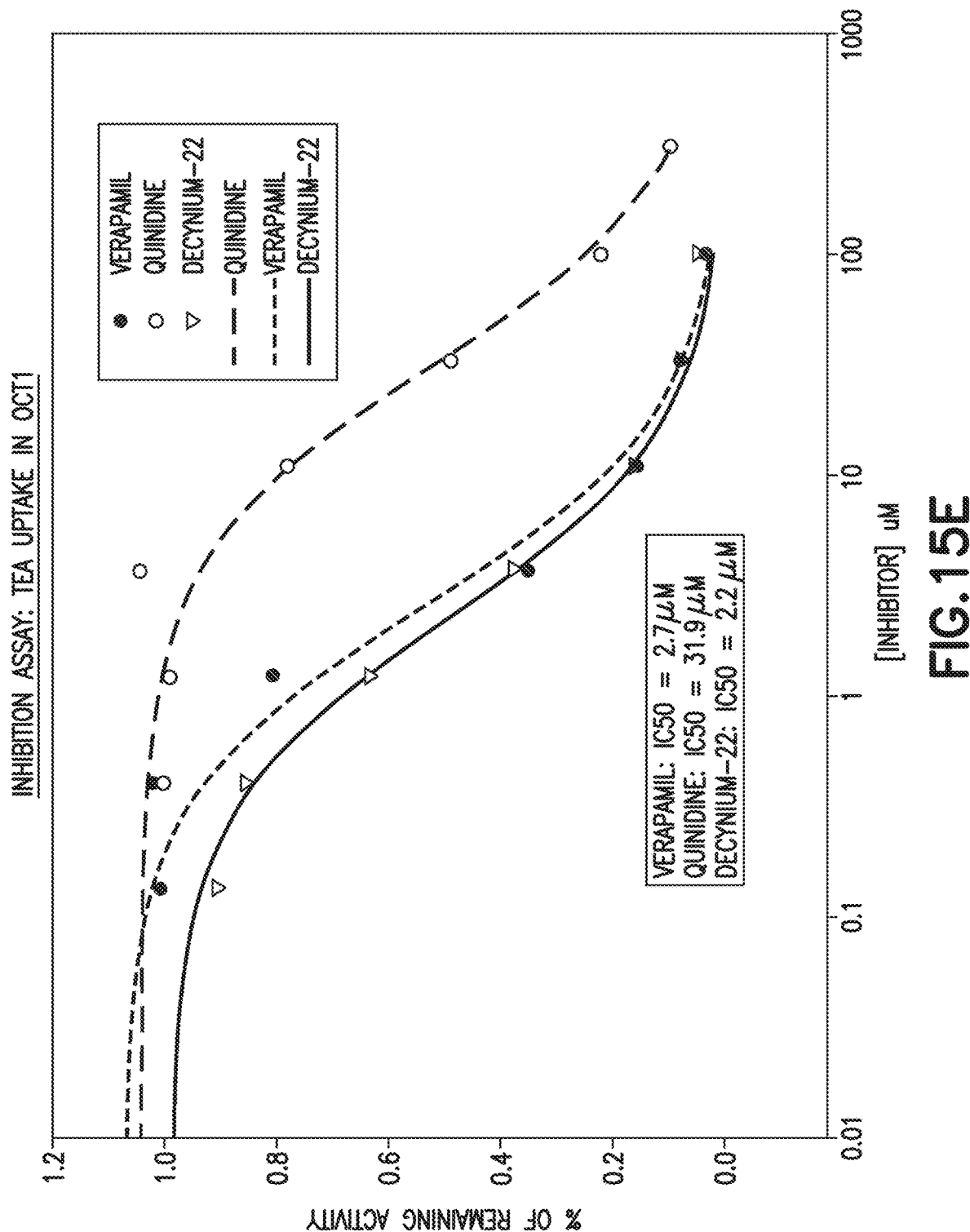

CONSUMABLE CRYOPRESERVED CELLS TRANSIENTLY OVEREXPRESSING GENE(S) ENCODING DRUG TRANSPORTER PROTEIN(S) AND/OR DRUG METABOLIZING ENZYME(S)

CROSS-REFERENCES TO RELATED APPLICATIONS

This application is filed under 35 U.S.C. § 111 as a continuation application of U.S. application Ser. No. 15/988,819, filed on May 24, 2018, which is a continuation application of U.S. application Ser. No. 15/688,983, now U.S. Pat. No. 10,047,136, filed on Aug. 29, 2017, which is a continuation application of U.S. application Ser. No. 14/972,012, now U.S. Pat. No. 9,822,160, filed on Dec. 16, 2015, which is a division of U.S. application Ser. No. 14/644,000, filed on Mar. 10, 2015, which is a continuation application of International Application No. PCT/US2013/059152, filed on Sep. 11, 2013, which designates the United States and claims priority to U.S. Provisional Patent Application No. 61/699,466, filed on Sep. 11, 2012, the entire contents of which are incorporated by reference herein.

FIELD OF THE INVENTION

The present invention relates to cryopreserved recombinant cells transiently overexpressing one or more genes encoding drug transporter protein and/or drug metabolizing enzyme such that activity of the encoded protein(s) is detectable in a population of said cells following thaw from cryopreservation.

BACKGROUND OF THE INVENTION

Drug development is a costly and time consuming endeavor whereby drug candidates must satisfy certain criteria established by government agencies such as the U.S. Food and Drug Administration and European Medicines Agency prior to receiving regulatory approval for marketing thereof. Importantly, assays are conducted to screen drug candidates to determine whether any are substrates or inhibitors of one or more drug transporter proteins and/or drug metabolizing enzymes as that can have a significant effect on the absorption, distribution, metabolism and elimination of such drugs, their toxicity and drug-drug interactions.

Although cell lines stably expressing a gene encoding a drug transporter proteins or a drug metabolizing enzyme may be used for such screening, significant time and resources are required to generate and maintain frozen stocks thereof. Plus, the level of recombinant protein expressed is typically variable (laboratory to laboratory) and may deteriorate and/or become more variable over time with passage of such cells. Alternatively, freshly plated cells either stably or transiently expressing a gene encoding a drug transporter protein or a drug metabolizing enzyme may be employed for such screening. However, freshly plated cells have a limited shelf life of a few days and are difficult to ship in a manner that maintains their viability. In addition, to generate stable cell lines, the foreign transfected gene is actually integrated into the host genome of the cells and carried along with it during cycles of cells division. The chromosomal integration in the host cells will lead to permanent modification of host genome, potentially leading to abnormal expression of other genes causing unexpected changes of host behavior and unreliable experimental results. Thus, there is a need for cells suitable for screening drug candidates that reduces the investment of time and resources associated with drug development and provide reliable results.

SUMMARY OF THE INVENTION

The present invention provides cryopreserved recombinant cells suitable for screening drug candidates to determine whether any are substrates or inhibitors of one or more drug transporter proteins and/or drug metabolizing enzymes that provide reliable results and ready convenience. Desirably, the level of activity in a population of the recombinant cells following cryopreservation is comparable to that of freshly transfected cells. Additionally, the cryopreserved recombinant cells are readily packaged in a vial and shipped with dry ice or dry shipper and conveniently stored at −135° C. in liquid nitrogen upon receipt with several years shelf life. Hence, such cells provide the end user a consumable "thaw and use" product which provides convenience in conducting experiments and reduces the investment of time and resources in creating and/or maintaining cell stocks for screening drug candidates.

In one aspect, the present invention provides cryopreserved recombinant cells including one or more transiently overexpressed genes encoding a protein selected from the group consisting of a drug transporter protein and a drug metabolizing enzyme, or a combination thereof wherein activity of the drug transporter protein or the drug metabolizing enzyme or combinations is detectable in a population of the cryopreserved recombinant cells following thaw from cryopreservation.

In another aspect, the present invention provides processes of preparing transiently transfected recombinant cells which transiently overexpresses one or more genes encoding a protein selected from a drug transporter protein and a drug metabolizing enzyme or a combination thereof including transiently transfecting cells with one or more genes encoding a drug transporter protein or a drug metabolizing enzyme and cryopreserving the transiently transfected recombinant cells within 48 hrs of transfection.

These and other features of the invention will be better understood through a study of the following detailed description.

BRIEF DESCRIPTION OF THE FIGURES

FIG. 15E is a graph depicting results of an inhibition assay whereby HEK293 cells overexpressing OCT1 were incubated with TEA and OCT1 inhibitor (quinidine, verapamil or decynium-22) at various concentrations in the range of 0.1-500 µM for 10 min.

DETAILED DESCRIPTION OF THE INVENTION

Figure 1:
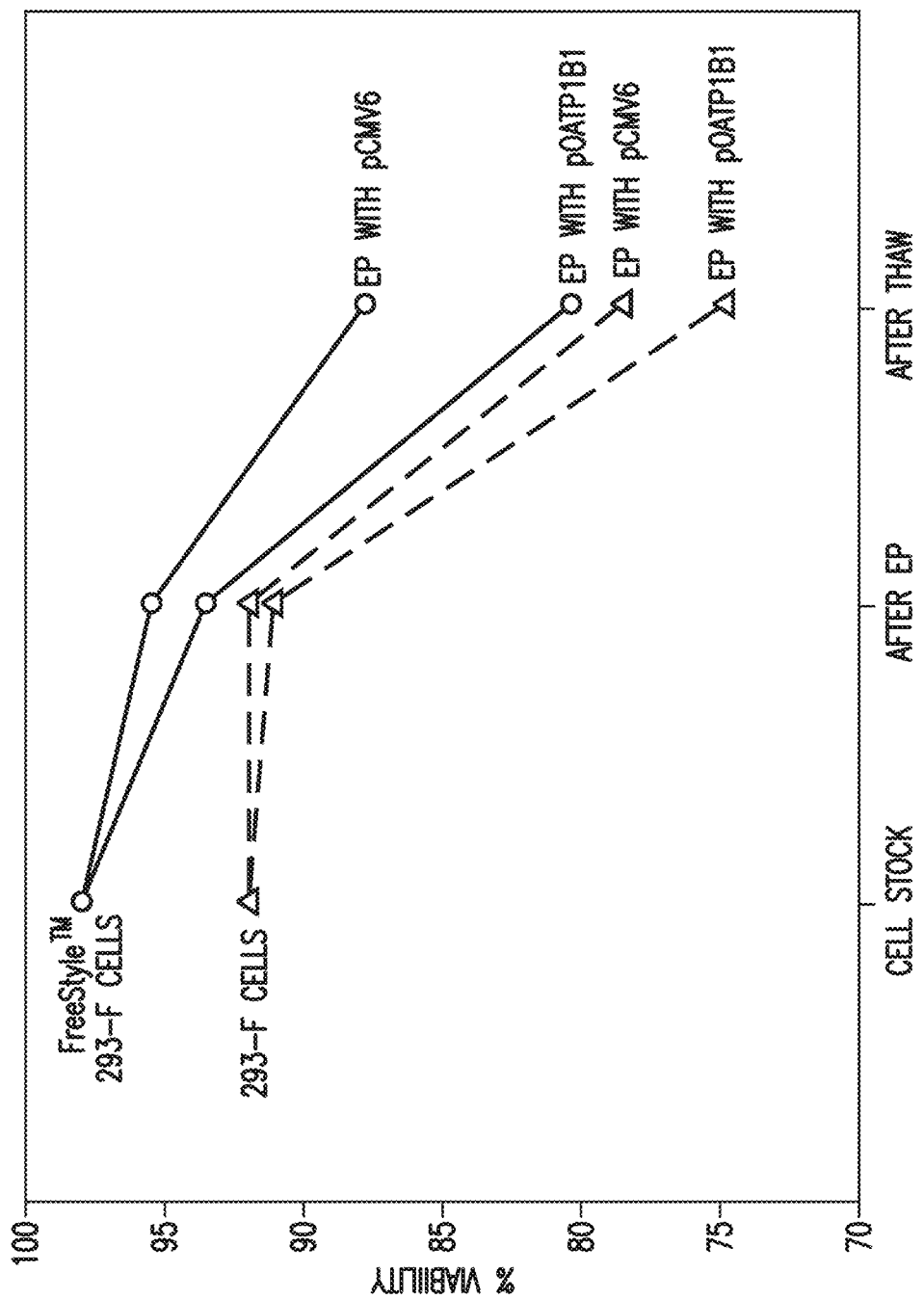
FIG. 1 is a graph of the percentage of viable cells from cell stock, cells after electroporation (EP) and cells after thaw from cryopreservation for FreeStyle™ 293-F (FS293) cells and 293-F cells grown in suspension.

As used herein the following terms shall have the definitions set forth below.

As used herein, the term "cell" includes both primary cells as well as established cell lines (e.g., human embryonic kidney HEK293 cells, Chinese hamster ovary CHO, Madin-Darby Canine Kidney Cells MDCK, Pig Kidney Epithelial Cells LLC-PK1, human epithelial colorectal adenocarcinoma cells Caco-2 and Chinese hamster lung fibroblast V79 cells).

As used herein, the term "drug transporter protein" refers to a membrane bound transport protein that includes, but is not limited to ATP binding cassette (ABC) transporters and solute carrier (SLC) transporters.

As used herein, the term "drug metabolizing enzyme" includes, but is not limited to, cytochromes such as cytochrome (CYP) P450; UDP-glucouronyl transferase and other non-CYP drug metabolizing enzymes such as alcohol dehydrogenase, monoamine oxidase and aldehyde oxidase.

As used herein, the term "detectable" means that the activity of a selected probe substrate in cells transfected with a drug transporter protein and/or drug metabolizing enzyme shall be higher than the activity of the same probe substrate in cells transfected with empty vector; desirably, the difference in activity will be at least 5-fold.

As used herein, the use of upper case letters in transporter nomenclature identifies the human protein/gene, i.e., MRP2/ABCC2, etc.; smaller case letters indicate the transporter derives from a preclinical (nonhuman mammalian) species, i.e., Mrp2/Abcc2, etc. Unless otherwise specified, a gene is derived from any species (e.g., human or other mammal).

As used herein, the terms "OATP1B1" "OATP2" and "SLCO1B1" are interchangeable and refer to a human protein/gene that corresponds to the nonhuman protein/gene Oatp2. Unless noted otherwise, reference to OATP1B1 is to OATP1B1*1b.

As used herein, the terms "OAT1" and "SLC22A6" are interchangeable and refer to an organic anion transporter 1.

Unless noted otherwise, reference to OAT1 is to the full length cDNA encoding with 563 amino acids (also referred to herein as "OAT1 long").

Exemplary ABC transporters include, but are not limited to those listed below in Table 1.

TABLE 1

| GENE NAME | PROTEIN NAME |
|---|---|
| MDR1/P-gp/ABCB1 | Multidrug Resistance Protein1 |
| MRP1/ABCC1 | Multidrug resistance protein 1 |
| MRP2/ABCC2 | Multidrug resistance-associated protein 2 |
| MRP3/ABCC3 | Multidrug resistance protein 3 |
| MRP4/ABCC4 | Multidrug resistance protein 4 |
| MRP5/ABCC5 | Multidrug resistance protein 5 |
| MRP6/ABCC6 | Multidrug resistance protein 6 |
| MRP7/ABCC7 | Multidrug resistance protein 7 |
| MRP8/ABCC8 | Multidrug resistance protein 8 |
| BCRP/ABCG2 | Breast Cancer Resistance Protein |
| BSEP/ABCB11 | Bile Salt Export Pump |

Exemplary SLC transporters include, but are not limited to those listed below in Table 2.

TABLE 2

| GENE NAME | PROTEIN NAME |
|---|---|
| OSTα | Organic solute transporter α |
| OSTβ | Organic solute transporter β |
| OATP1B1*/SLCO 1B1/OATP2 | Organic anion-transporting polypeptide 1B1 |
| OATP1B3/SLCO 1B3 | Organic anion-transporting polypeptide 1B3 |
| OAT1/SLC22A6 | Organic anion transporter 1 |
| OAT2/SLC22A7 | Organic anion transporter 2 |
| OAT3/SLC22A8 | Organic anion transporter 3 |
| OAT4/SLC22A11 | Organic anion transporter 4 |
| OCT1/SLC22A1 | Organic cation transporter 1 |
| OCT2/SLC22A2 | Organic cation transporter 2 |
| OCT3/SLC22A3 | Organic cation transporter 3 |
| OATP1A2/SLCO1A2 | Organic anion-transporting polypeptide 1A2 |
| OATP2B1/SLCO2B1 | Organic anion-transporting polypeptide 2B1 |
| PEPT1/SLC15A1 | Peptide Transporter 1 |
| PEPT2/SLC15A2 | Peptide Transporter 2 |
| OCTN1/SLC22A4 | Organic cation/ergothioneine transporter |
| OCTN2/SLC22A5 | Organic cation/carnitine transporter |
| MATE1/SLC47A1 | Multidrug and toxin extrusion 1 |
| MATE2K/SLC47A2 | Multidrug and toxin extrusion 2K |
| URAT1/SLC22A12 | Urate Transporter 1 |
| ASBT/SLC10A2 | Apical sodium/bile acid co-transporter |
| NTCP/SLC10A1 | Sodium/taurocholate co-transporting peptide |

*In this instance, OATP1B1 includes OATP1B1*1a and OATP1B1*1b.

Exemplary SLC transporters tested, but are not limited to those listed below in Table 3.

TABLE 3

| GENE NAME | FULL NAME | GENE ACCESSION |
|---|---|---|
| OATP1B1*1a/ SLCO1B1*1a | Organic anion-transporting polypeptide 1B1 Wild Type (388A) | NM_006446.4 |
| OATP1B1*1b/ SLCO1B1*1b | Organic anion-transporting polypeptide 1B1 SNP 388A>G | NM_006446.3 |
| OATP1B3/SLCO1B3 | Organic anion-transporting polypeptide 1B3 | NM_019844 |
| OAT1/SLC22A6 | Organic anion transporter 1 | NM_004790 |
| OAT3/SLC22A8 | Organic anion transporter 3 | NM_004254 |
| OCT1/SLC22A1 | Organic cation transporter 1 | NM_003057 |
| OCT2/SLC22A2 | Organic cation transporter 2 | NM_003058 |

Cells suitable for use in the present invention include mammalian cells, for example, as derived from human or non-human (e.g., mouse, rat, dog, monkey, hamster and pig, etc.). In certain embodiments, the cells are hepatocytes, or endothelial cells.

Gene delivery systems for introducing gene(s) into a population of cells are known to a skilled artisan. Virus-based gene delivery methods may be used but require special handling of the cells due to safety concerns. Although lipid-based transfection methods may be used, lipid-based transfection reagents are relatively costly and such methods are not amenable to large-scale manufacturing processes. Additionally, lipid-based transfection methods result in relatively low gene delivery efficiency and relatively delayed protein expression (generally 72 to 96 hours post transfection) (data not shown). Electroporation (EP) is preferable as it is amenable to large-scale manufacturing processes and avoids the safety issues of viral-based gene delivery methods. Further, EP results in relatively efficient gene delivery.

After gene delivery into a population of cells, gene(s) encoding a drug transporter protein and/or a drug metabolizing enzyme will be overexpressed such that activity of the protein(s) encoded therefrom are detectable following thaw from cryopreservation. Drug candidates can be tested to determine if any are substrates or inhibitors of the protein(s) encoded from the overexpressed gene(s) by incubation of the recombinant cells therewith. In particular, if a drug candidate is a substrate of a drug transporter protein and/or a drug metabolizing enzyme, the drug candidate will be affected. For instance, if the drug candidate is a substrate of a drug transporter protein, the drug candidate will be translocated in or out of the recombinant cell via the drug transporter protein. However, if the drug candidate is an inhibitor of the drug transporter protein, the drug candidate will inhibit translocation of a substrate of the drug transporter protein in or out of the recombinant cell.

Alternatively, assays can be conducted using whole cells or subcellular fractions thereof (microsome/cytosol).

Additionally, recombinant cells of the present invention may be further transfected with RNAi or siRNA of the transiently overexpressed gene(s) to knockdown/knockout the expression thereof as is desirable for certain assays. Primary cells (e.g., hepatocytes) can be transfected with RNAi or siRNA directed against any ABC transporters, SLC transporters or any other drug metabolizing enzymes to knockdown/knockout the expression of specific genes.

In one aspect (1), the disclosure provides a cryopreserved recombinant cell including one or more transiently overexpressed genes encoding a protein selected from the group consisting of a drug transporter protein and a drug metabolizing enzyme, or a combination thereof wherein activity of the drug transporter protein or the drug metabolizing enzyme or combinations is detectable in a population of the cryopreserved recombinant cell following thaw from cryopreservation.

In an aspect (2), the disclosure provides the invention of aspect (1), wherein said one or more genes encodes a drug metabolizing enzyme.

In an aspect (3), the disclosure provides the invention of aspect (2), wherein the drug metabolizing enzyme is selected from the group consisting of cytochrome P450, UDP-glucouronyl transferase, alcohol dehydrogenase, monoamine oxidase and aldehyde oxidase.

In an aspect (4), the disclosure provides the invention of aspect (1), which transiently overexpresses one or more genes encoding a protein selected from the group consisting of an ATP binding cassette transporter and a solute carrier transporter protein.

In an aspect (5), the disclosure provides the invention of aspect (4), wherein said one or more genes is selected from the group consisting of MDR1/Mdr1a/Mdr1b, MRP1/Mrp1, MRP2/Mrp2, MRP3/Mrp3, MRP4/Mrp4, MRP5/Mrp5, MRP6/Mrp6, MRP7/Mrp7, MRP 8/Mrp8, BCRP/Bcrp, BSEP/Bsep, OATP2/Oatp2, OATP1B3/Oatp1b3, OAT1/Oat1, OAT2/Oat2, OAT3/Oat3, OAT4/Oat4, OCT1/Oct1, OCT2/Oct2, OATP1/Oatp1, PEPT1/Pept1, PEPT2/Pept2, OCTN1/Octn1, OCTN2/Octn2, MATE1/Mate1, MATE2K/Mate2, URAT1/Urat1, ASBT/Asbt, and NTCP/Ntcp.

In an aspect (6), the disclosure provides the invention of aspect (4), wherein said one or more genes encodes a protein that is an ATP binding cassette transporter selected from the group consisting of MDR1/Mdr1a/Mdr1b, MRP1/Mrp1, MRP2/Mrp2, MRP3/Mrp3, MRP4/Mrp4, MRP5/Mrp5, MRP6/Mrp6, MRP7/Mrp7, MRP 8/Mrp8, BCRP/Bcrp, and BSEP/Bsep.

In an aspect (7), the disclosure provides the invention of aspect (4), wherein said one or more genes encodes a protein that is a solute carrier transporter selected from the group consisting of OATP2/Oatp2, OATP1B3/Oatp1b3, OAT1/Oat1, OAT2/Oat2, OAT3/Oat3, OAT4/Oat4, OCT1/Oct1, OCT2/Oct2, OCT3/Oct3, OATP1/Oatp1, PEPT1/Pept1, PEPT2/Pept2, OCTN1/Octn1, OCTN2/Octn2, MATE1/Mate1, MATE2K/Mate2, URAT1/Urat1, ASBT/Asbt, and NTCP/Ntcp.

In an aspect (8), the disclosure provides the invention of aspect (4), wherein said one or more genes is selected from OATP1B1*1a, OATP1B1*1b, OATP1B3, OAT1, OAT3, OCT1, OCT2, MATE1 and MATE2K.

In an aspect (9), the disclosure provides the invention of aspect (1), wherein the one or more genes is derived individually from human or an animal species selected from mouse, rat, guinea pig, dog, and monkey.

In an aspect (10), the disclosure provides the invention of aspect (1), wherein said cell is derived from a mammal.

In an aspect (11), the disclosure provides the invention of aspect (10), wherein said cell is selected from the group consisting of HEK293, CHO, MDCK, LLC-PK1, Caco-2 and V79 cells.

In an aspect (12), the disclosure provides the invention of aspect (10), wherein the mammal is selected from the group consisting of human, monkey, dog, rat, mouse, porcine and hamster.

In an aspect (13), the disclosure provides the invention of aspect (1), wherein said cell comprises a hepatocyte.

In an aspect (14), the disclosure provides the invention of aspect (1), wherein said cell comprises an endothelial cell.

In an aspect (15), the disclosure provides the invention of aspect (1), wherein activity of the protein(s) is detectable in a population of said cell at least 24 hours post plating following thaw from cryopreservation.

In an aspect (16), the disclosure provides the invention of aspect (1), wherein activity of the protein(s) is detectable in a population of said cell at least 48 hours post plating following thaw from cryopreservation.

In an aspect (17), the disclosure provides the invention of aspect (1), wherein activity of the protein(s) is detectable in a population of said cell at least 72 hours post plating following thaw from cryopreservation.

In another aspect (18), the disclosure provides a process of preparing transiently transfected recombinant cells which transiently overexpresses one or more genes encoding a protein selected from a drug transporter protein and a drug metabolizing enzyme including transiently transfecting cells with one or more genes encoding a drug transporter protein or a drug metabolizing enzyme and cryopreserving the transiently transfected recombinant cells within 48 hrs of transfection.

In an aspect (19), the disclosure provides the invention of aspect (18), wherein the transient transfection step includes electroporation.

EXAMPLES

Cells were cultured under standard sterile practices for cell culture, and transiently transfected using EP. Following EP, cells were assayed for protein activity both before as well as after being frozen, thawed and plated. As detailed below, cells cultured in suspension and adherent cell cultures were both successfully transiently transfected and exhibited substantial activity of the recombinant protein following thaw from cryopreservation.

Cells Cultured in Suspension

In brief, on Day 1, FreeStyle 293 Cells and 293-F cells were each passaged into appropriate sized shaker flasks at a density of 0.7-1.0×10$^6$ cell/ml using supplemented CD293 medium (i.e., CD293 medium (available from Gibco, Cat. No. 11913-019, Life Technologies Corp., Carlsbad, Calif.) supplemented with 4 mM L-Glutamine (available from Gibco, Cat. No. 25030-081, Life Technologies Corp., Carlsbad, Calif.)) or supplemented Excell™ 293 serum free media (available from Sigma, Cat. No. 14571C, Sigma-Aldrich, St. Louis, Mo.) supplemented with 6 mM L-Glutamine. Cell viability and cell number were determined using a Cellometer (available from Nexcelom Bioscience, Lawrence, Mass.).

On Day 2, EP of cells was executed. In short, following a determination of cell viability and cell density, cells were pelleted down by spinning at 100 g for 5 min, after which the media was aspirated and cells resuspended in 30 ml EP Buffer (available from MaxCyte, Cat. No. B201, MaxCyte Inc., Gaithersburg, Md.). The cell suspension was transferred to 50 ml Falcon tubes, pelleted down as described above, and resuspended in an appropriate amount of EP Buffer to reach 100×10$^6$ cells/ml which was used as the cell stock. DNAs to be used for EP were 15 prepared in sterile water at a final concentration of 5 mg/ml. For each sample, 0.4 ml of cell stock and DNA was placed in a sterile 1.5 ml eppendorf tube resulting in a final concentration of 200 µg/ml (Table 4) or 300 µg/ml DNA (Table 10 and Table 11) and cell density of 40×10$^6$ cells per sample.

TABLE 4

| SAMPLE # | CELL TYPE | PLASMID(S) | CELL STOCK VOL. (ml) | [DNA] (ug/ml) |
|---|---|---|---|---|
| A | 1, 2 | FS293 | pOATP1B1 | 0.4 | 200 |
| B | 3, 4 | | pCMV6 | 0.4 | 200 |
| C | 5 | | EP Buffer (16 µl) | 0.4 | — |
| D | 6, 7 | 293-F | pOATP1B1 | 0.4 | 200 |
| E | 8, 9 | | pCMV6 | 0.4 | 200 |
| F | 10 | | EP Buffer (16 µl) | 0.4 | — |

Samples were transferred into an OC-400 Processing Assembly (available from MaxCyte, Cat. No. OC-400R, MaxCyte Inc., Gaithersburg, Md.) which followed the manufacture instructions for EP of HEK cells. Following EP, the cells were carefully pipetted out and transferred into the bottom of a 125 ml shaker flask and incubated for 20 min at 37° C. with 8% CO$_2$, after which pre-warmed 40 ml CD293 media was added into the shaker flask to reach cell density at $1\times10^6$ cells/ml. The cells were incubated for 30 min at 37° C. and 8% $CO_2$. After 30 min recovery, cell viability and cell density were determined. A portion of cells (i.e., $20\times10^6$ cells) was used for plating and the rest was cryopreserved, or all of the cells were cryopreserved. It is contemplated that recombinant cells may be cryopreserved within 48 hrs of transfection and exhibit activity of protein(s) encoded from transfected gene(s) at a detectable level following thaw from cryopreservation.

For plating cells following EP, $20\times10^6$ cells were pelleted down by spinning at 100 g for 5 min and then resuspended in 20 ml pre-warmed plating media (DMEM with high glucose (available from Gibco, Cat. No. 11965092, Life Technologies Corp., Carlsbad, Calif.), supplemented with 0.1 mM non-essential amino acids (available from Gibco, Cat. No. 11140050, Life Technologies Corp., Carlsbad, Calif.), 10% FBS (available from SAFC Biosciences, Cat. No. 12016C, Sigma, St. Louis, Mo.)) (cell density of $1\times10^6$ cells/ml). Cells were placed in 24-well tissue culture plates poly-D-Lysine coated, Corning Biocoat™ (available from Corning Life 16 Sciences, Tewksbury, Mass.) at a density of $0.2\times10^6$ cells/well and $0.4\times10^6$ cells/well and incubated at 37° C. with 8% $CO_2$ so as to determine the impact of seeding density on uptake activity. Media was replaced 4 hours later and then every 24 hours until the day of assaying. On Days 4, cells were assayed for OATP1B1 activity as described below.

For cryopreservation, cells were pelleted then resuspended in freshly prepared ice-cold freezing media (9 parts supplemented CD293 medium and 1 part DMSO which was syringe filtered to sterilize) at a density of $10\times10^6$ cell/ml. Cryo vials were filled with 1 ml of this cell suspension, and placed on ice-cold Mr Frosty freezing container (available from Thermal Scientific), which was stored in −80° C. freezer overnight after which the vials were transferred into liquid nitrogen.

Cryopreserved cells were assayed for OATP1B1 activity as described below. In brief, on Day 1, cryopreserved cells were removed from liquid nitrogen to dry ice, and then thawed in a water bath at 37° C. for about 2 min. Cells were transferred into 10 ml of plating media as described above which is pre-warmed to a temperature of about 37° C. and the viability and cell density determined. Cells were pelleted down and resuspended in supplemented DMEM media at a cell density of $1\times10^6$ viable cells/ml. Cells were plated in the same manner described above for plating cells following EP (which had not been cryopreserved) and assayed for OATP1B1 activity at 24, 48 and 72 hrs following plating thereof.

Adherent Cell Cultures

In brief, HEK293 cells were cultured in 5 Layer Corning® CellStack® (available from Corning Inc. Life Sciences, Tewksbury, Mass.) using plating media containing DMEM (high glucose) available from Gibco Cat. No. 11965118, Life Technologies Corp., Carlsbad, Calif.; Penicillin-Streptomycin (10,000 units/ml) available from Gibco Cat. No. 15140-122, Life Technologies Corp., Carlsbad, Calif.; L-Glutamine (200 mM) available from Gibco Cat. No. 25030-081, Life Technologies Corp., Carlsbad, Calif.; Sodium Pyruvate, available from Gibco Cat. No. 11360, Life Technologies Corp., Carlsbad, Calif.; FBS available from Sigma-Aldrich Corp., St. Louis, Mo. in a ratio of 100:1:1:1:10. On Day 1, about 24 hrs before EP, HEK293 cells were trypsinized, cell viability and cell number determined after which cells were passaged to fresh multilayer chamber flasks at 30-40% confluency. Cells were incubated at 37° C. with 5% $CO_2$.

On Day 2, EP of cells was executed. In short, cells were harvested, cell viability and cell number determined after which cells were pelleted down by spinning at 100 g for 5 min and the media aspirated. Cells were resuspended in EP buffer and pelleted down by spinning at 100 g for 5 min, then resuspended in an appropriate amount of EP Buffer to reach $50\times10^6$ cells/ml which was used as the cell stock. DNAs to be used for EP were prepared in sterile water at a final concentration of 5 mg/ml. For each sample used for OC-400 processing assembly, 0.4 ml of cell stock and DNA was placed in a sterile 1.5 ml eppendorf tube resulting in a final concentration of 50 µg/ml, 100 µg/ml, 200 µg/ml or 400 µg/ml DNA as indicated in FIGS. 5-9 and cell density of $40\times10^6$ cells per sample. For each sample used for CL-2 processing assembly, 10 ml of cell stock and DNA was placed in 50 ml sterile conical tube resulting in a final concentration of 100 µg/ml DNA.

Samples were transferred into an OC-400 or CL-2 processing assembly (available from MaxCyte, Cat. No. OC-400R and CL2-R, MaxCyte Inc., Gaithersburg, Md.) which followed the manufacture instructions for EP of HEK cells. Following EP, the cells were carefully pipetted out and transferred into 6-well tissue culture plates and incubated for 20 min at 37° C. with 5% $CO_2$, after which cells were removed and placed in a 50 ml conical tube containing pre-warmed plating media. Cell viability and cell density were determined. A portion of cells (i.e., $20\times10^6$ cells) was used for plating and the rest was cryopreserved.

For plating cells following EP, cells were pelleted down by spinning at 100 g for 5 min and then resuspended in pre-warmed plating media (cell density of $1\times10^6$ cells/ml). Cells were placed in 24-well tissue culture plates (poly-D-Lysine coated, Corning Biocoat™ (available from Corning Life Sciences, Tewksbury, Mass.)) at a density of $0.4\times10^6$ cells/well and incubated at 37° C. with 5% $CO_2$. Media was replaced 4 hours later and then every 24 hours until the day of assaying. On Days 4 and 6, cells were assayed for OATP1B1 activity.

For cryopreservation, cells were pelleted then resuspended in freshly prepared ice-cold freezing media (9 parts plating medium and 1 part DMSO which was syringe filtered to sterilize) at a density of $10\times10^6$ cell/ml. Cryo vials were filled with 1 ml of this cell suspension, and placed on ice-cold Mr Frosty freezing container (available from Thermal Scientific) stored in −80° C. freezer overnight after which the vials were stored in liquid nitrogen.

Cryopreserved cells were assayed for OATP1B1 activity. Notably, cells were plated in the same manner described above for plating cells following EP (which had not been cryopreserved) and assayed for OATP1B1 activity (as described below) at 48 hrs following plating thereof.

Assaying Transporter Activity

In brief, substrate solution was prepared for OATP1B1*1a and OATP1B1*1b using 2 µM estradiol-17β-glucuronide (99% of cold E17βG and 1% of [$^3$H]-E17βG); for OATP1B3 using 2 µM CCK-8 (99% of cold CCK-8 and 1% of [$^3$H]-CCK-8); for OAT1 short using 1 µM Para-aminohippurate (PAH) (90% of cold PAH and 10% of [$^3$H]-PAH); for OAT1 long using 1 µM or 3 µM Para-aminohippurate (PAH) (90% of cold PAH and 10% of [$^3$H]-PAH); for OAT3 using 1 µM or 2 µM Estrone-3-sulfate (99% of cold E3S and 1% of [$^3$H]-E3S); for OCT1 and OCT2 using 30 µM Tetraethylammonium Bromide (100% [$^{14}$C]-TEA); for MATE1 and MATE2K using 10 µM Metformin (100%

[$^{14}$C]-Metformin) or 10 μM Tetraethylammonium Bromide (100% [$^{14}$C]-TEA); in Krebs-Henseleit Buffer pH 7.4 (available from Sigma, Cat. No. K3753, Sigma-Aldrich, St. Louis, Mo.) and incubated at 37° C. for at least 20 min. Culture media was aspirated from cells to be assayed and cells washed thrice with pre-warmed KHB Buffer. Cells were subsequently incubated with Uptake Buffer at 37° C. for 10 min. For MATE1 and MATE2K, cells were washed and pre-incubated with KHB buffer containing 20 mM NH$_4$Cl for 10 min Assays were initiated by adding 0.3 ml substrate solution into each well and incubated at 37° C. for 5 min with samples for OCT1 and OCT2 incubated for 10 min.

The reaction was quickly stopped after the incubation period by aspirating substrate solution from cells then washing cells thrice with cold Uptake Buffer. Cells were then incubated with lysing solution (0.1% SDS with 0.1% v/v 1M NaOH in Dulbecco's Phosphate-Buffered Saline (DPBS) buffer) for 15-20 minutes while being shaken. The substrate solution was triturated and 0.4 ml of the resultant cell lysis placed in 5 ml scintillation tube with 5 ml of scintillation liquid for analysis with scintillation counter.

As illustrated in FIG. 1, cell viability dropped 1-5% after EP relative to that of the cell stock. Additionally, after cryopreservation, cell viability dropped an additional 10-15% relative to that after EP. Nonetheless, even after EP and thaw from cryopreservation, cell viability is greater than 75%.

Cell morphology and uptake activity was examined following cryopreservation after 30 min recovery and 24 hrs recovery post transfection. Table 5 illustrated cell morphology and uptake activity with 24 hrs recovery was reduced compared to 30 min recovery.

TABLE 5

|  | Recovery time prior | Cell Confluency | Uptake Activity |  |
| --- | --- | --- | --- | --- |
| OATP1B1 | 24 HOURS | 40-50% | 0.59 | 0.44 |
| OATP1B1 | 30 MIN | 70-75% | 5.78 | 4.32 |
| VECTOR | 30 MIN | 90-95% | 1.34 |  |

Figure 2:
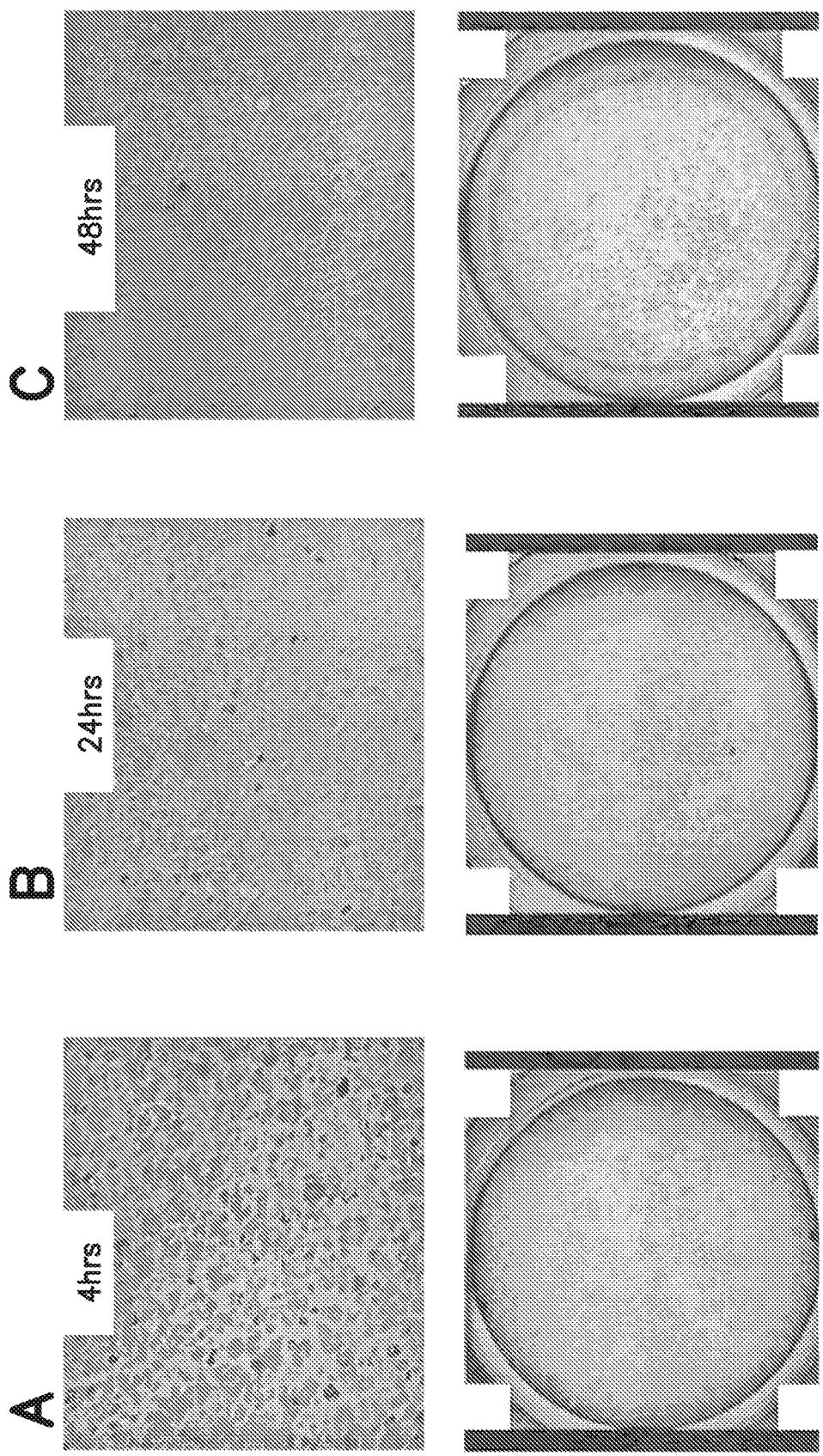
FIG. 2 are images of transfected cells 4 hrs (A), 24 hrs (B) and 48 hrs (C) after plating following thaw from cryopreservation.

Cell morphology and confluency of transfected cells thawed from cryopreservation were examined after various periods of time following plating at a density of 0.4×10$^6$ cells per well in 24-well poly-D-lysine coated Corning Biocoat™ plates. In particular, FIG. 2 illustrates OATP1B1 transiently transfected cells cultured at 4 hrs, 24 hrs and 72 hrs post plating. Additionally, cell confluency at 24 hrs, 48 hrs and 72 hrs post-plating of these cells is recorded in Table 6 below.

TABLE 6

| CELLS | 24 hrs | 48 hrs | 72 hrs |
| --- | --- | --- | --- |
| FS293 with pOATP1B1 | 80-90% | 90-95% | 80-85% |
| FS293 with pCMV6 vector | 70-80% | 90-95% | 90% |
| 293-F with pOATP1B1 | 90-95% | 95-100% | 80-85% |
| 293-F with pCMV6 vector | 90-95% | 95-100% | 80-85% |

Figure 4:
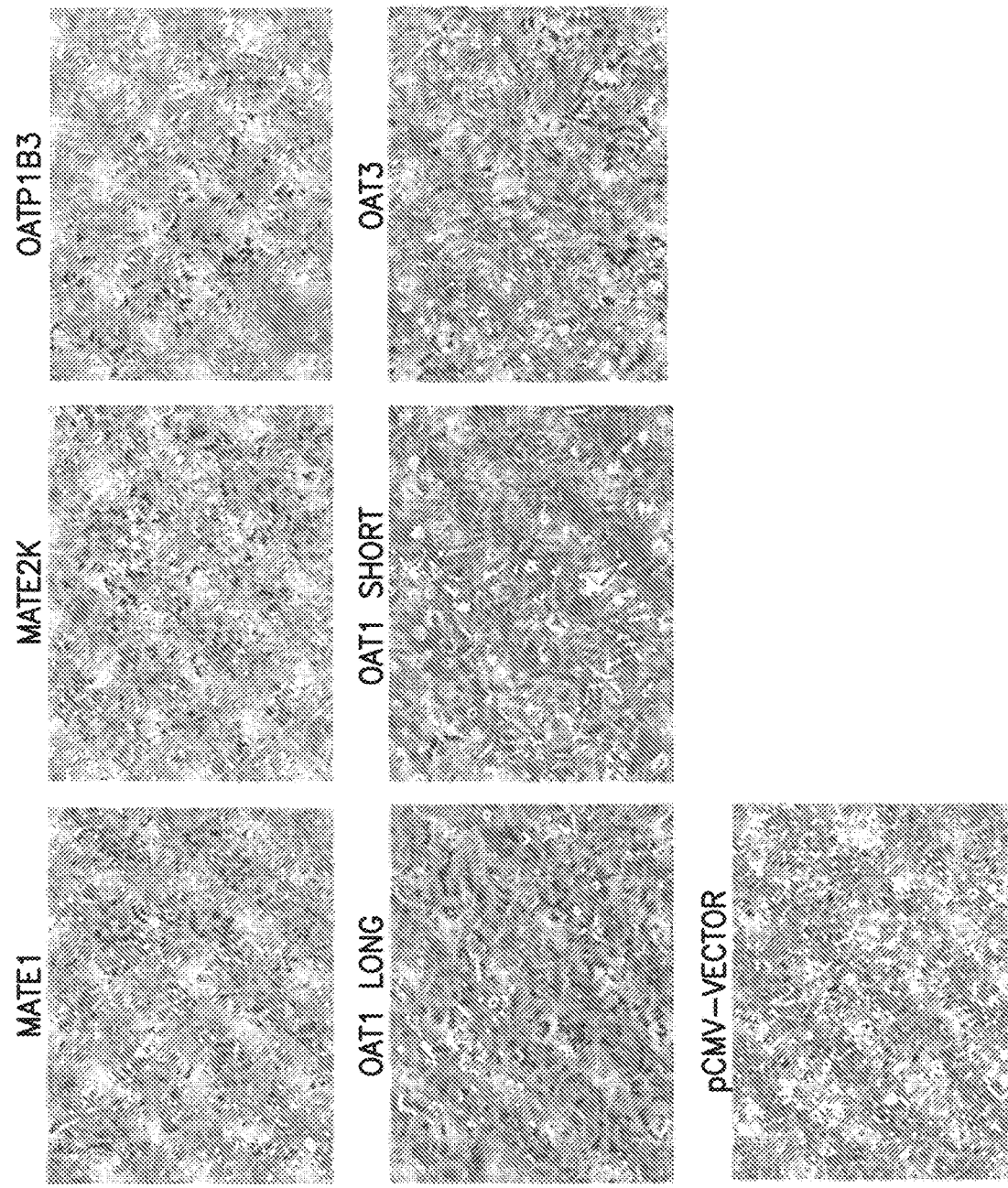
FIG. 4 are images of 293-F cells transfected with MATE1, MATE2K OATP1B3, long isoform OAT1 (full length cDNA with 563 amino acids; referred to herein as "OAT1 long"), short isoform OAT1 (missing 13 amino acid at C-terminus 522-534, with 550 amino acids; referred to herein as "OAT1 short"), OAT3, and pCMV vector plated at $0.4 \times 10^6$ cells per well in 24-well poly-D-lysine coated plates at 24 hrs post-plating (following thaw from cryopreservation).

Desirably, after EP and cryopreservation, the cells form a monolayer on poly-D-lysine coated Corning Biocoat™ plates achieving 80-90% confluency at 24 hrs post-plating, 90%-100% confluency at 48 hrs post-plating FIG. 4 illustrates cells, transiently transfected with MATE1, MATE2K, OATP1B3, OAT1 long, OAT1 short, OAT3, and pCMV vector respectively, cultured at 24 hrs post plating after thawed from cryopreservation.

Figure 5:
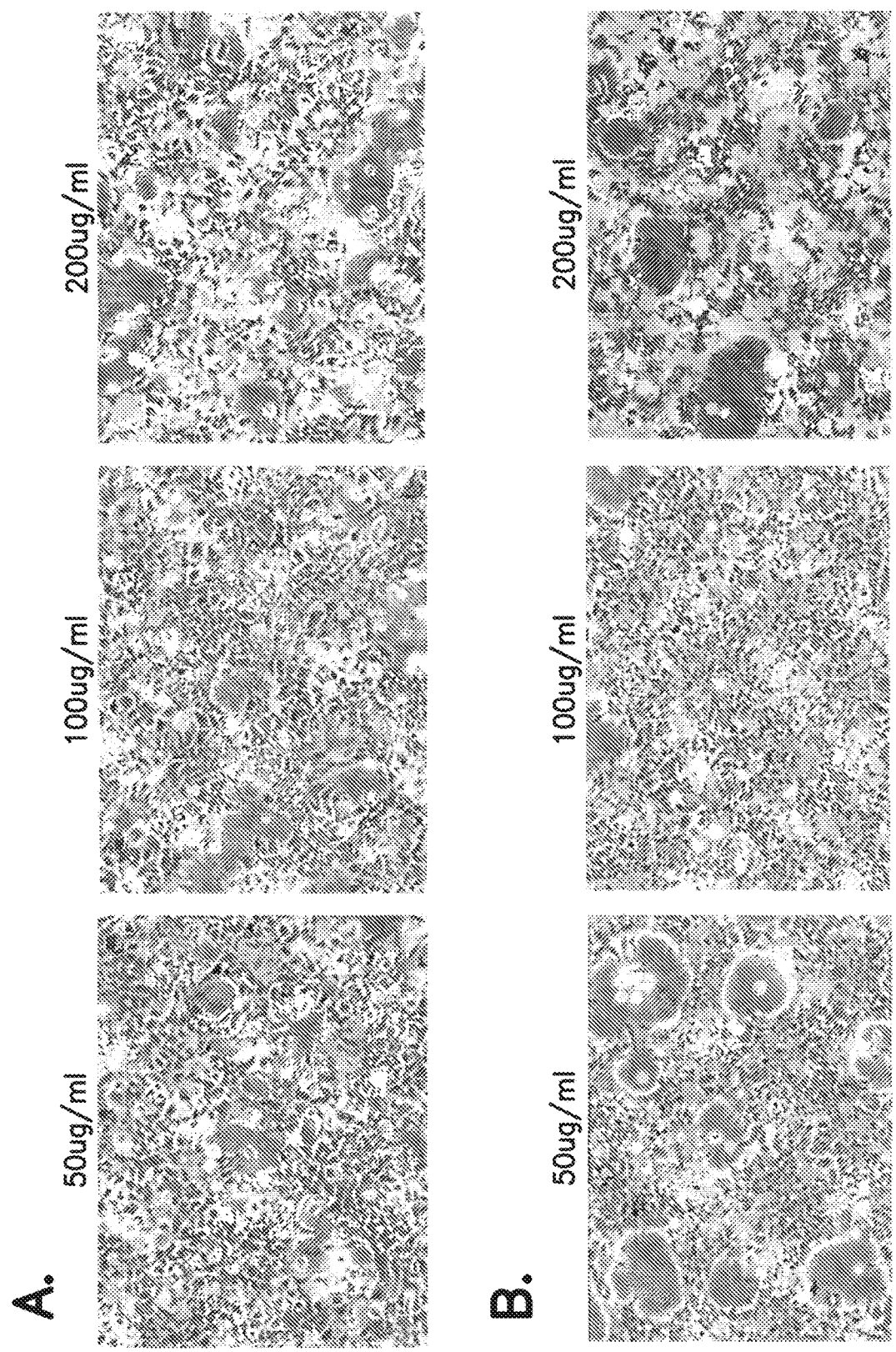
FIG. 5 are fluorescence images of adhered HEK293 cells transfected with 50 µg/ml, 100 µg/ml or 200 µg/ml green fluorescent protein (GFP) 24 hrs (A) and 48 hrs (B) following EP.

As illustrated in FIG. 5, the expression of Green Fluorescent Protein (GFP) in adhesion HEK293 cells was increased with increasing concentration of DNA. Additionally, GFP expression increased at the 48 hr timepoint relative to the 24 hr timepoint. In particular, GFP transfection efficiency by EP achieved 100% at 24 hrs with 200 μg/ml DNA and 100% fluorescent cell staining at 48 hrs with 100 μg/ml DNA. Hence, GFP protein expression level in transfected cells increased with increased DNA concentration and at 48 hrs relative to 24 hrs.

Uptake activity of suspension cultured 293 cells transfected with OATP1B1 (pOATP1B1) and control vector (pCMV) were assayed at various time points following EP. In brief, transfected cells were plated at a density of 0.4×10$^6$ cells/well in 24-well poly-D-lysine coated Corning Biocoat™ plates following EP or after thaw from cryopreservation. OATP1B1 uptake activity and uptake ratio were determined using probe substrate, estradiol-17β-glucuronide, in both fresh plated cells ("fresh") and cryopreserved cells ("cryo") at various timepoints post plating as detailed in Table 7 below.

TABLE 7

| CELLS/ CULTURE MEDIA, FRESH OR CRYO | CELL PLATING TIME POINT (HR) | UPTAKE ACTIVITY (pmol/mg/min)/confluence | | UPTAKE RATIO |
| --- | --- | --- | --- | --- |
| | | pOATP1B1 | pCMV | |
| 293-F in CD293, fresh | 48 | 15.4 (85%) | 0.7 (90%) | 22.0 |
| 293-F in CD293, cryo | 48 | 15.1 (95-100%) | 0.9 (95-100%) | 16.8 |
| FS293 in Excell, cryo | 24 | 36.4 | 1.9 | 19.2 |
| | 48 | 10.0 | 0.7 | 14.3 |
| | 72 | 6.6 | 1.0 | 6.6 |
| 293-F in CD293, cryo | 24 | 27.4 | 1.5 | 18.3 |
| | 48 | 15.1 | 0.9 | 16.8 |
| | 72 | 9.9 | 1.0 | 9.9 |

Note:
The number appearing in parentheses is the cell confluency at assay time.

OATP1B1 uptake activity and uptake ratio in transfected cells following thaw from cryopreservation is consistent with those in freshly plated transfected cells. In both cells types 293-F and FS293, the highest uptake activity and uptake ratio is observed at 24 hrs post plating.

Figure 3:
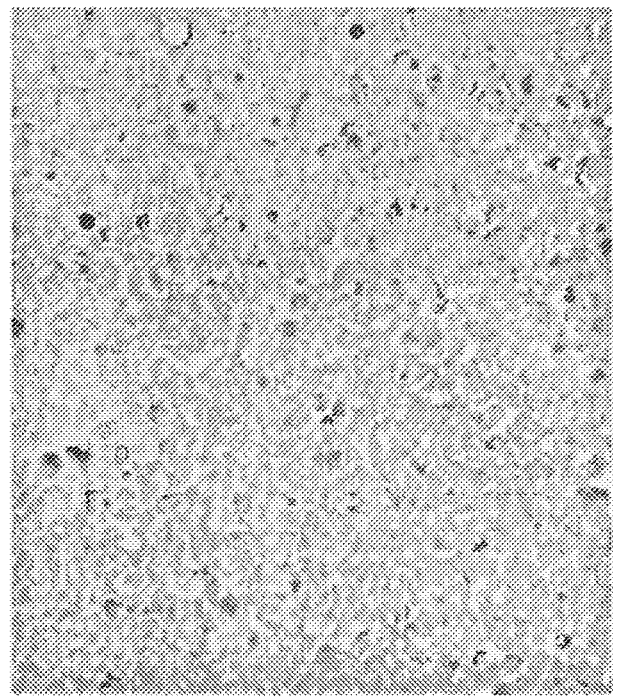
FIG. 3 are images of 293-F cells transfected with pOATP1B1 expression plasmid plated at (A) $0.4 \times 10^6$ viable cells per well and (B) $0.2 \times 10^6$ viable cells per well in 24-well poly-D-lysine coated plates and cultured in plating media at 24 hrs post-plating (following thaw from cryopreservation).
Figure 3:
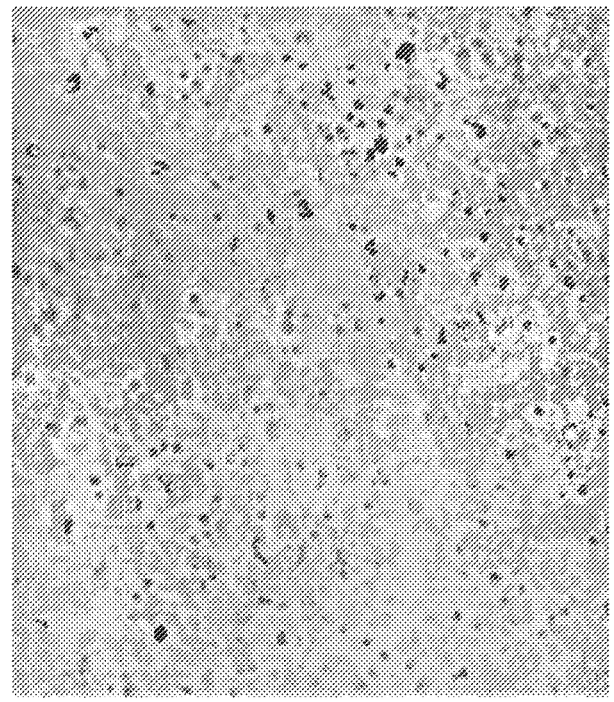

Morphology and cell confluency of transfected cells (FS293 or 293-F) were examined at 24 hrs, 48 hrs and 72 hrs post-plating in 24-well poly-D-lysine coated Corning Biocoat™ plates at plating density of either 0.4×10$^6$ cells/well or 0.2×10$^6$ cells/well after thaw from cryopreservation. Cell confluency at 24 hrs post-plating are summarized below in Table 8. Cell confluency at 48 hrs and 72 hrs are similar to those achieved at 24 hrs (data not shown). Additionally, FIG. 3 provides images of transfected cells plated at (A) 0.4×10$^6$ cells per well and (B) 0.2×10$^6$ cells per well 24 hrs post-plating following thaw from cryopreservation at a confluence of 90-95% and 60-70%, respectively.

TABLE 8

| CELLS, CULTURE MEDIA, TRANSFECTED DNA | 0.4 × 10$^6$ CELLS/WELL | 0.2 × 10$^6$ CELLS/WELL |
| --- | --- | --- |
| FS293 with pOATP1B1 in Excell | 80-90% | 30-50% |
| FS293 with pCMV vector in Excell | 70-80% | 50% |

TABLE 8-continued

| CELLS, CULTURE MEDIA, TRANSFECTED DNA | $0.4 \times 10^6$ CELLS/WELL | $0.2 \times 10^6$ CELLS/WELL |
|---|---|---|
| 293-F with pOATP1B1 in CD293 | 90-95% | 60-70% |
| 293-F with pCMV6 vector in CD293 | 90-95% | 80% |

For optimal assay performance, plating cells at a density of $0.4 \times 10^6$ is preferable to that of $0.2 \times 10^6$ as it achieves higher cell confluency and higher uptake activity.

TABLE 9

| | UPTAKE ACTIVITY (pmol/mg/min)/ confluence | | UPTAKE |
|---|---|---|---|
| CELLS | pOATP1B1 | pCMV6 | RATIO |
| FS293 cells, $0.2 \times 10^6$ cells/well | 10.5 | 3.0 | 3.5 |
| FS293 cells, $0.4 \times 10^6$ cells/well | 36.4 | 1.9 | 19.2 |
| 293-F cells, $0.2 \times 10^6$ cells/well | 20.2 | 1.5 | 13.5 |
| 293-F cells, $0.4 \times 10^6$ cells/well | 27.4 | 1.5 | 18.3 |

Following EP, cell viability was examined using trypan blue and hemocytometer or cellometer.

Figure 6:
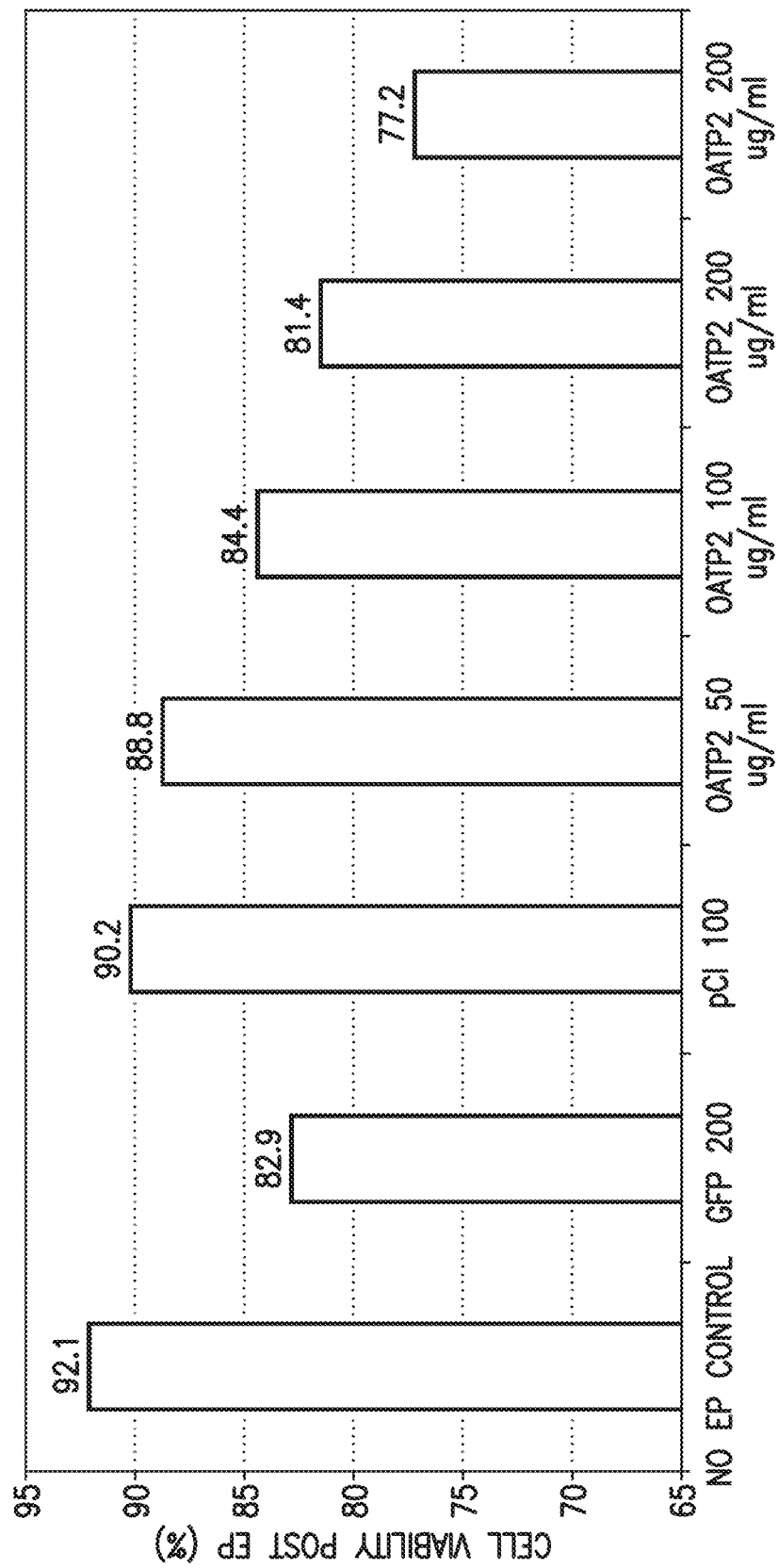
FIG. 6 is a graph of the percentage of viable cells following EP of adhered HEK293 cells using varying amounts of DNA.

As illustrated in FIG. 6, when using adhesion HEK293 cells, cell viability post EP dropped with increasing amounts of DNA used in EP. Nonetheless, cell viability following transfection with pOATP1B1 was ranged from 89% to 77% and that following transfection with empty vector was 90%.

Figure 7A:
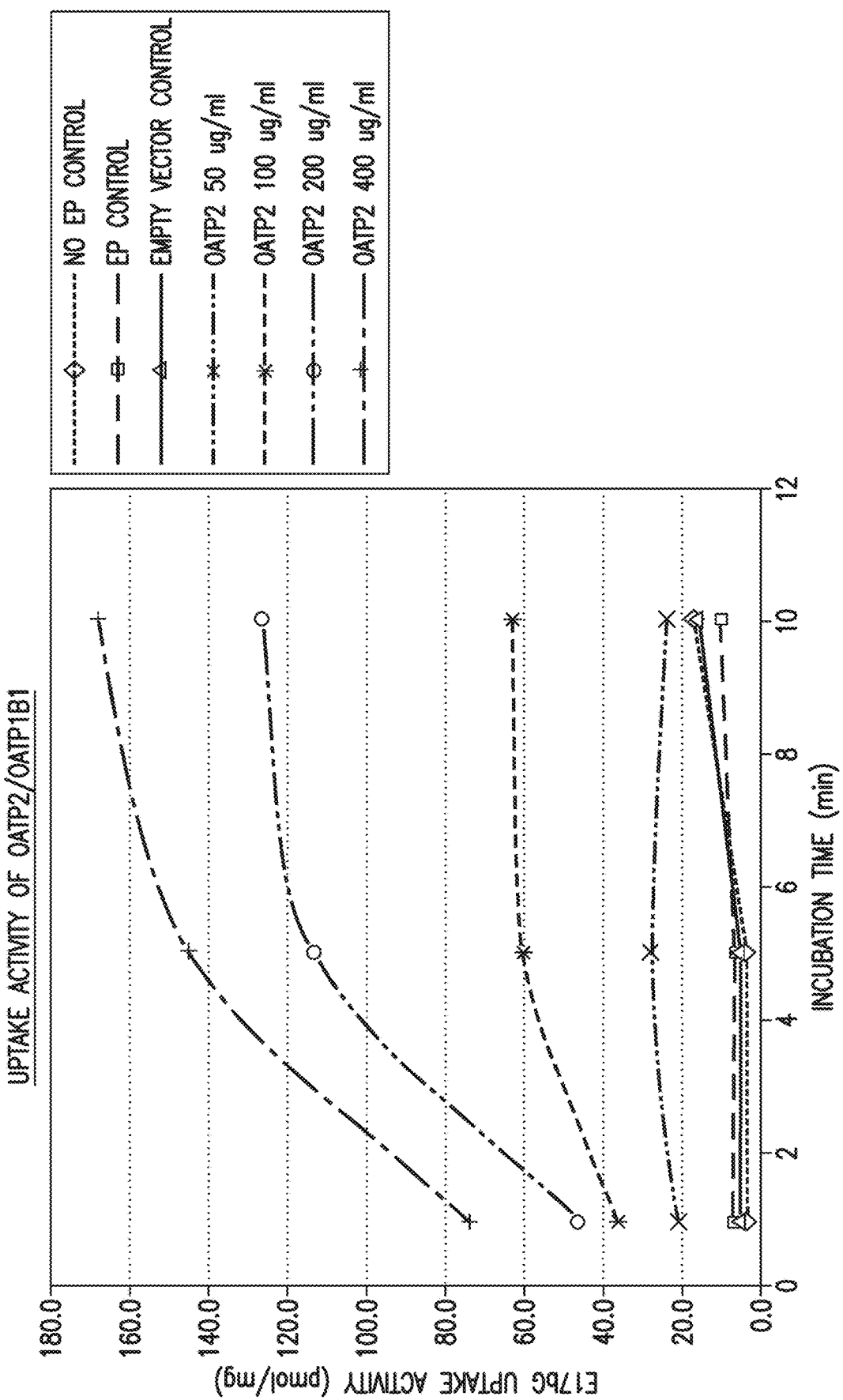
FIG. 7A is a graph of estradiol-17β-glucuronide (E17βG) uptake activity following various incubation times in adhered HEK293 cells transfected with varying amounts of DNA (i.e., 0, 50 µg/ml, 100 µg/ml, 200 µg/ml or 400 µg/ml OATP2/OATP1B1) at 48 hrs post EP.
Figure 7B:
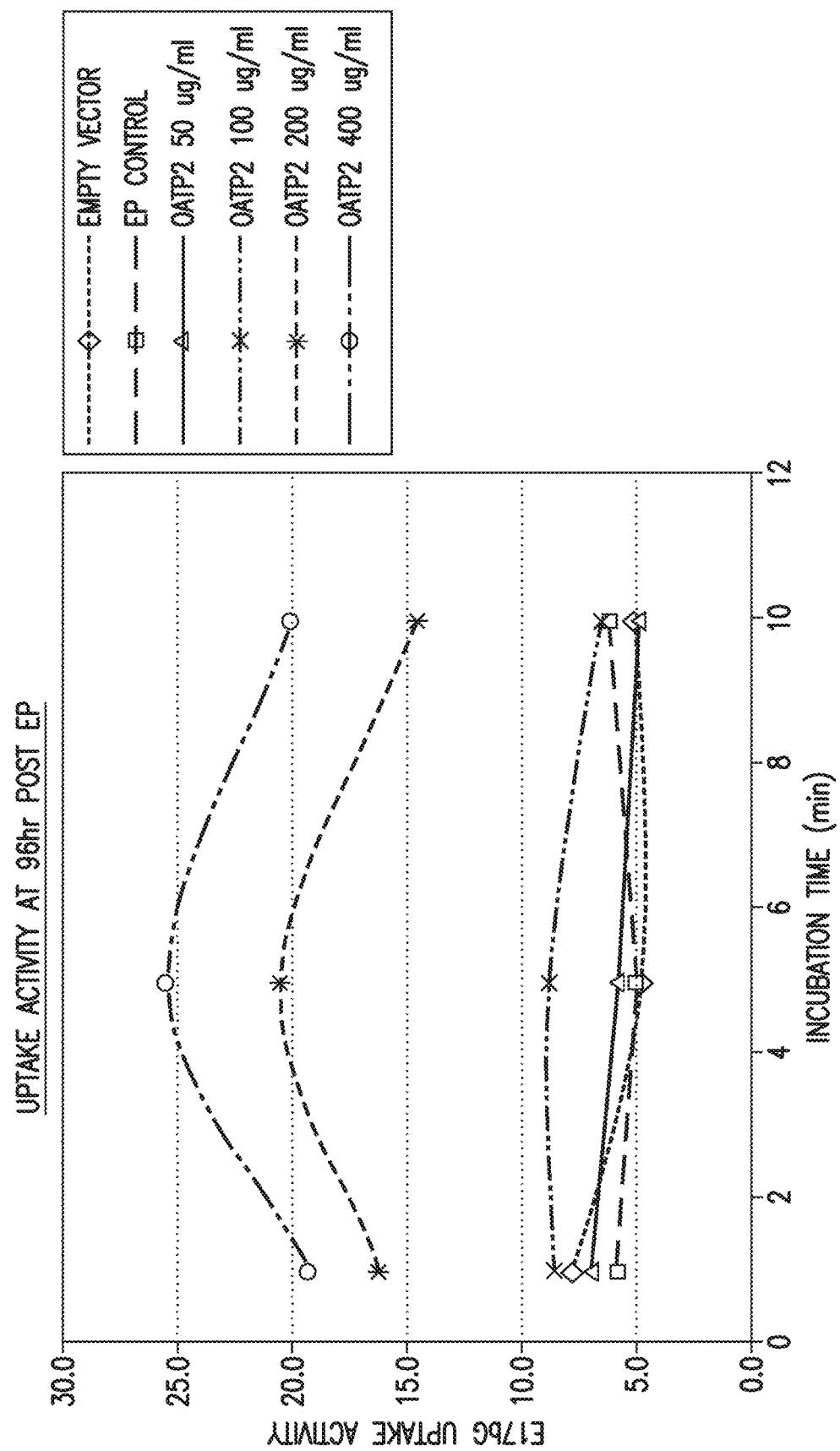
FIG. 7B is a graph of estradiol-17β-glucuronide (E17βG) uptake activity following various incubation times in adhered HEK293 cells transfected with varying amounts of DNA (i.e., 0, 50 µg/ml, 100 µg/ml, 200 µg/ml or 400 µg/ml OATP2/OATP1B1) at 96 hrs post EP.
Figure 8:
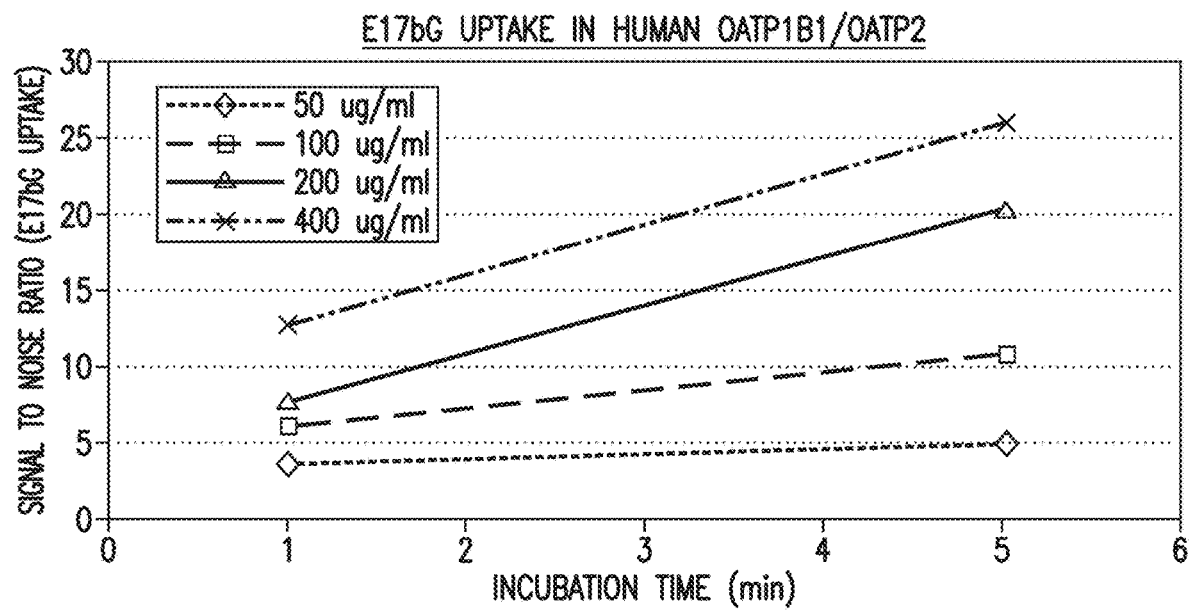
FIG. 8 is a graph of signal to noise ratio of estradiol-17β-glucuronide (E17βG) uptake following various incubation times in adhered HEK293 cells transfected with varying amounts of DNA (i.e., 0, 50 µg/ml, 100 µg/ml, 200 µg/ml or 400 µg/ml OATP2/OATP1B1) at 48 hrs post EP.

As illustrated in FIG. 7, when using adhesion HEK293 cells, OATP1B1 mediated uptake of Estradiol-17β-glucuronide in the fresh plated transient transfected adhesion HEK293 cells is time-dependent. Notably, uptake activity and uptake ratio increased with increasing amounts of DNA used in EP. However, OATP1B1 mediated uptake of Estradiol-17β-glucuronide reduced at the 96 hr timepoint relative to the 48 hr timepoint. Further, as illustrated in FIG. 8, the signal to noise ratio (i.e., uptake ratio) of estradiol-17β-glucuronide increased with the increase of amount of DNA and assay incubation time, in adhesion HEK293 cells transfected with OATP1B1 relative to empty vector at 48 hrs post EP.

Figure 9:
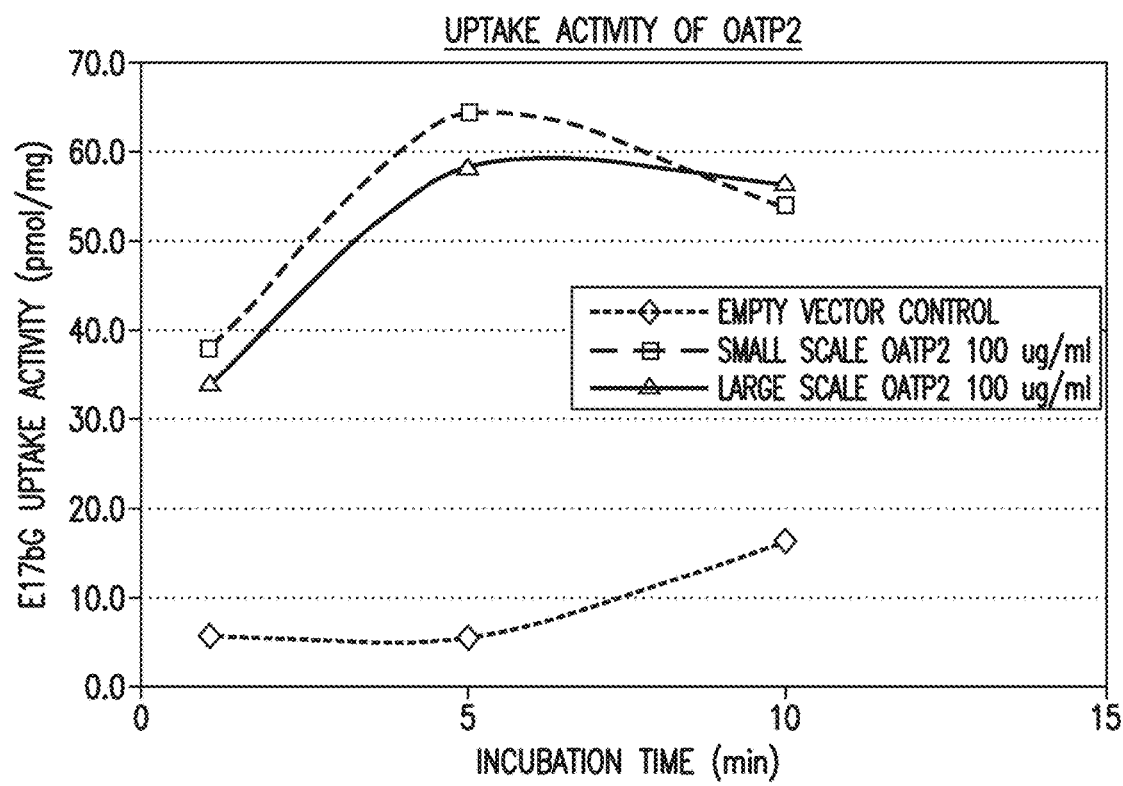
FIG. 9 is a graph of estradiol-17β-glucuronide (E17βG) uptake activity in adhered HEK293 cells transfected with either OATP2/OATP1B1 using a small scale EP device (OC400), OATP2/OATP1B1 using a large scale EP device (CL2), or an empty vector control.

As illustrated in FIG. 9, when using adhesion HEK293 cells, estradiol-17β-glucuronide uptake in OATP1B1 transiently expressed HEK293 cells using small scale EP device and large scale EP device is consistent for both uptake activity and signal to noise ratio (i.e., uptake ratio). 100 μg/ml DNA was used in the experiments.

Figure 10:
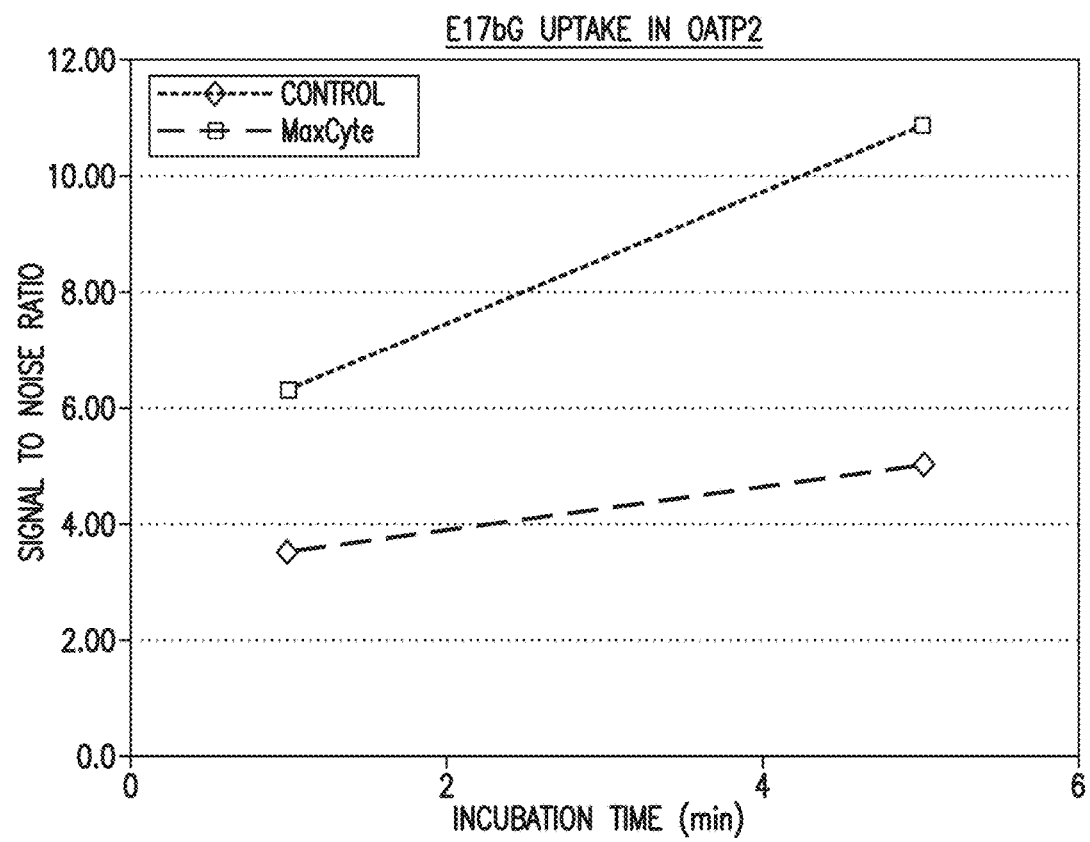
FIG. 10 is a graph of signal to noise ratio of estradiol-17β-glucuronide (E17βG) uptake following various incubation times in adhered HEK293 cells transfected with OATP1B1 gene using either "Control" (i.e., traditional lipid transfection reagent (lipofectamine 2000, available from Invitrogen)) or STX, MaxCyte scalable EP device.

As illustrated in FIG. 10, when using adhesion HEK293 cells, OATP1B1 uptake activity is compared between the cells transfected using traditional lipid transfection reagent (control: lipofectamine 2000, available from Invitrogen) and EP using STX, MaxCyte Inc., Gaithersburg, Md. Notably, cells transfected using EP resulted in a pronouncedly greater signal to noise ratio relative to those cells transfected with lipid transfection reagent.

Figure 11:
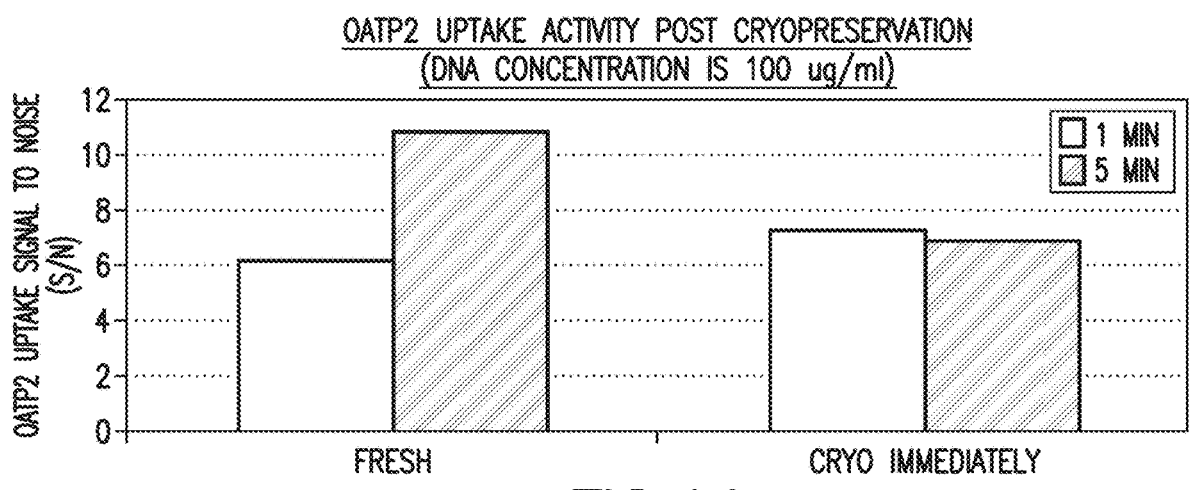
FIG. 11 is a graph of signal to noise ratio of estradiol-17β-glucuronide (E17βG) uptake following various incubation times in adhered HEK293 cells transfected with OATP1B1 that are freshly plated or plated following thaw from cryopreservation.

As illustrated in FIG. 11, when using adhesion HEK293 cells, OATP1B1 uptake activity in both freshly plated EP transfected cells and cells following thaw from cryopreservation was detectable.

Uptake activity of suspension cultured 293 cells transfected with OATP1B1*1a, OATP1B1*1b, OATP1B3, OAT1 long, OAT1 short, OAT3, OCT1, OCT2, MATE1, MATE2K or control vector (pCMV) were assayed at 24 hrs post plating after thaw from cryopreservation. In brief, the transfected cells were plated at a density of $0.4 \times 10^6$ cells/well in 24-well poly-D-lysine coated Corning Biocoat™ plates following EP and after thaw from cryopreservation. SLC transporter uptake activity and uptake ratio were determined using probe substrates as indicated at 24 hrs post plating as detailed in Table 10 below.

TABLE 10

| | | UPTAKE ACTIVITY (pmol/mg/min)/ | | |
|---|---|---|---|---|
| TRANSPORTERS | SUBSTRATE | SLC transporter | pCMV6 | UPTAKE RATIO |
| OATP1B1*1a | 2 μM E17bG | 41.0 | 1.03 | 40 |
| OATP1B1*1b | 2 μM E17bG | 32.6 | 0.88 | 37 |
| OATP1B3 | 2 μM CCK-8 | 28.7 | 0.2 | 145 |
| OATP1B3 | 2 μM CCK-8 | 77.0 | 0.79 | 98 |
| OAT1 long | 1 μM PAH | 13.1 | 0.3 | 39 |
| OAT1 short | 1 μM PAH | 9.7 | 0.3 | 29 |
| OAT1 long | 3 μM PAH | 15.0 | 0.71 | 21 |
| OAT3 | 1 μM E3S | 44.7 | 1.2 | 38 |
| OAT3 | 2 μM E3S | 60.9 | 1.62 | 38 |
| OCT1 | 30 μM TEA | 127.6 | 5.63 | 23 |
| OCT2 | 30 μM TEA | 100.5 | 5.53 | 18 |
| MATE1 | 10 μM Metformin | 71.4 | 6.0 | 12 |
| | 10 μM TEA | 46.3 | 4.3 | 11 |
| MATE2K | 10 μM Metformin | 33.5 | 5.2 | 6.5 |
| | 10 μM TEA | 46.6 | 6.1 | 7.6 |

As reflected in Table 10 above, the recombinant cells exhibited strong uptake activity towards their specific prototypical substrate each of which had an uptake ratio above 10. Notably, an uptake ratio above 5 indicates a successful process.

As reflected in Table 11, the post-thaw viability for recombinant cryopreserved cells was determined to be above 90%.

TABLE 11

| Cells | Post-thaw Viability |
|---|---|
| OATP1B1*1a | 94.2% |
| OATP1B1*1b | 96.1% |
| OATP1B3 | 95.5% |
| OAT1 long | 93.5% |
| OAT3 | 93.8% |
| OCT1 | 95.1% |
| OCT2 | 96.1% |

Each of these recombinant cells as well as a control vector (pCMV) was examined 24 hrs post-plating (after cryopreservation). Confluency for each of these cells 24 hrs post-plating was 85% or greater as reflected in Table 12 below.

TABLE 12

| Transfected Cells | 24-h confluency |
|---|---|
| OATP1B1*1a | 90% |
| OATP1B1*1b | 95% |
| OATP1B3 | 95% |
| OAT1 long | 90% |
| OAT3 | 90% |
| Vector | 95% |
| OCT1 | 95% |
| OCT2 | 85% |

Figure 12:
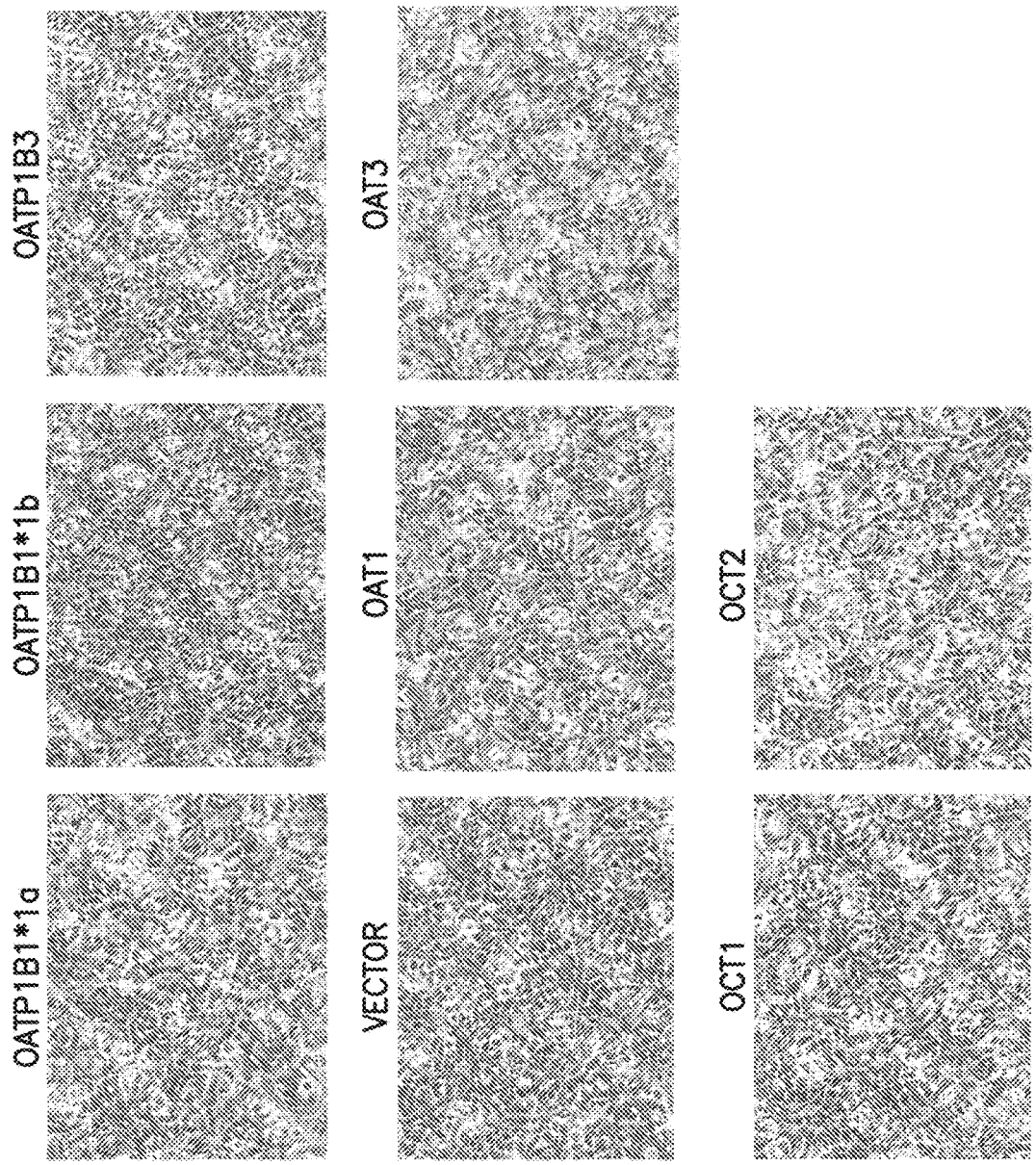
FIG. 12 are images of HEK293 cells transfected with OATP1B1*1a (Gene Accession No. NM_006446.4), OATP1B1*1b (Gene Accession No. NM_006446.3), OATP1B3, pCMV vector, long isoform OAT1 (full length cDNA with 563 amino acids), OAT3, OCT1 or OCT2 using MaxCyte scalable EP device and scale-up process followed by cryopreservation, thawing, plating on Poly-D-Lysine plates and incubation for 24 hrs post-plating.
Figure 13A:
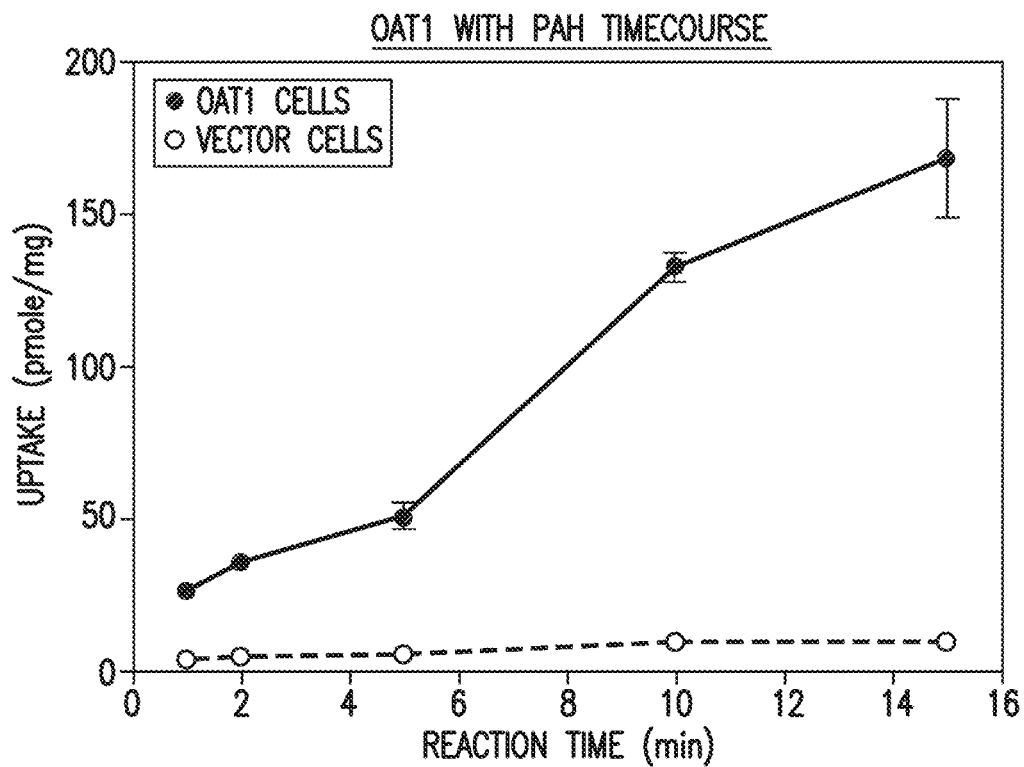
FIG. 13A is a graph depicting results of a time-dependent assay of p-Aminohippuric acid (PAH) (prototypical substrate for OAT1) uptake in HEK293 cells overexpressing OAT1 or pCMV vector following various incubation times (i.e., 1, 2, 5, 10 and 15 min.) with PAH at a concentration of 3 µM.
Figure 13B:
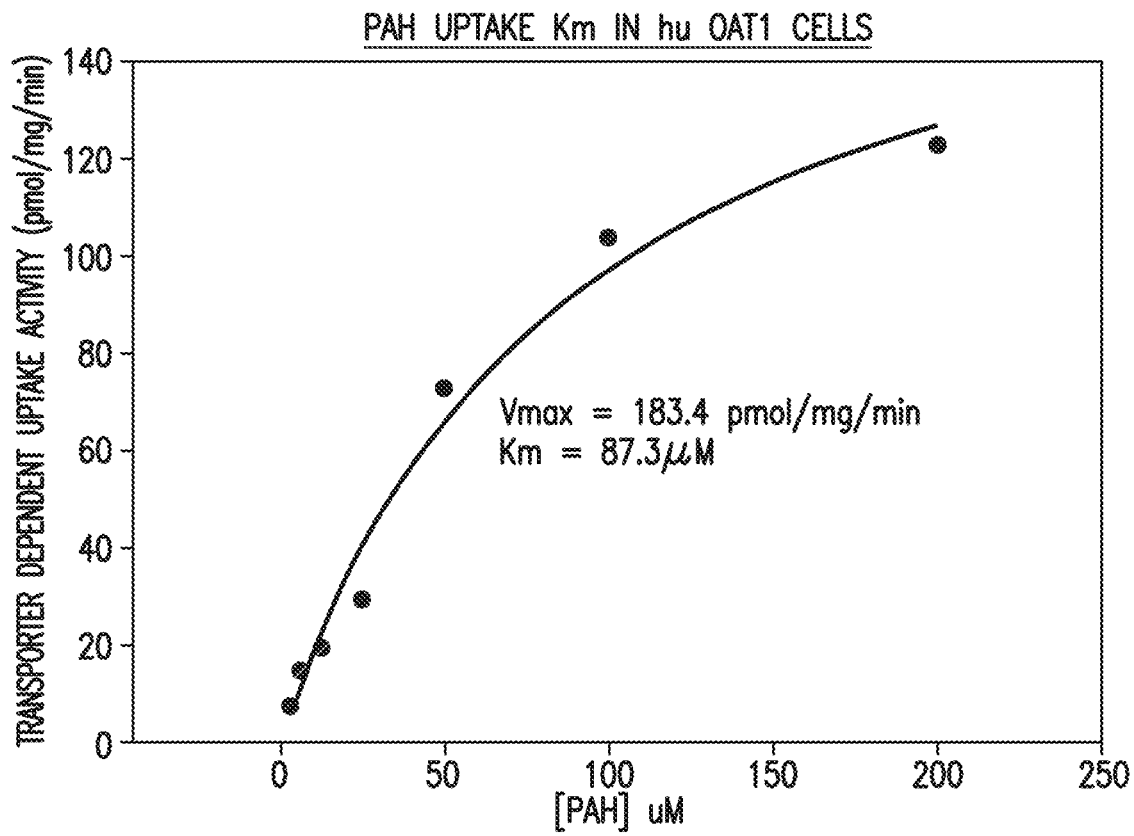
FIG. 13B is a graph depicting results of a kinetic assay whereby uptake of PAH at a concentration in the range of 3 to 200 µM was measured in HEK293 cells overexpressing OAT1 following incubation for 5 min. Km and Vmax, calculated using Sigma-plot, are shown as insert in the graph.
Figure 13C:
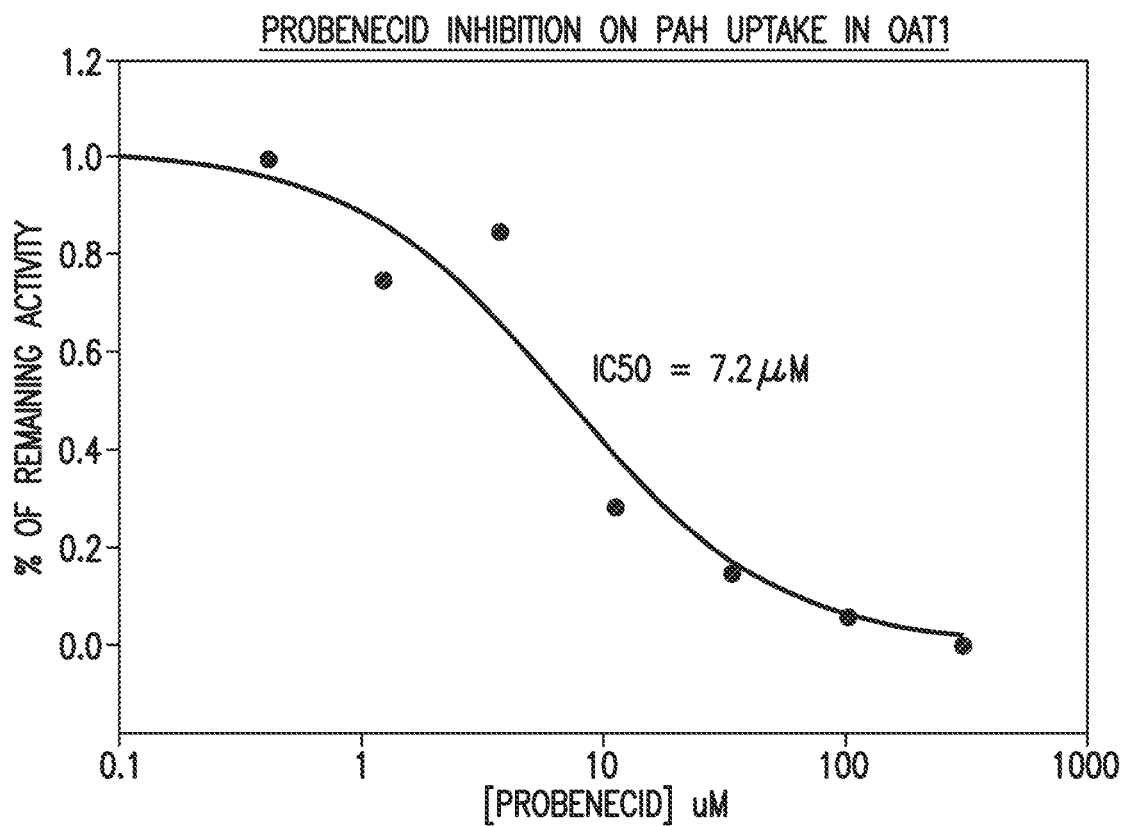
FIG. 13C is a graph depicting results of an inhibition assay whereby HEK293 cells overexpressing OAT1 were incubated with PAH at a concentration of 15 µM and probenecid (OAT1 inhibitor) at a concentration in the range of 0-300 µM for 5 min. IC50, calculated using Sigma-plot, is shown as insert in the graph.
Figure 14A:
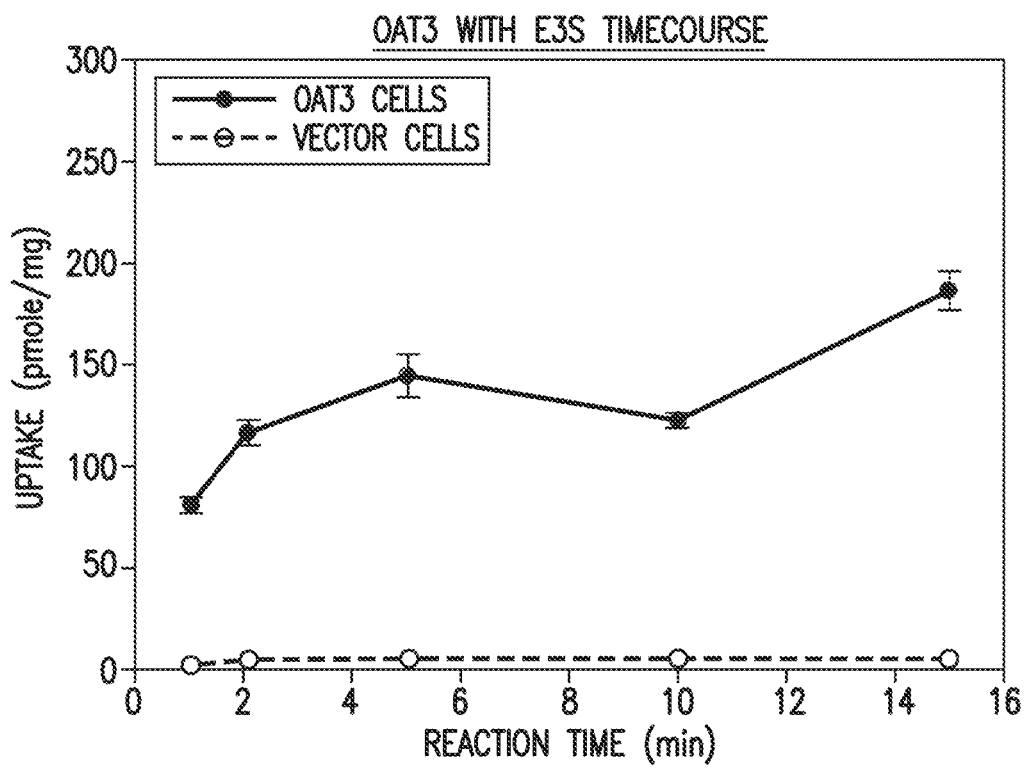
FIG. 14A is a graph depicting results of a time-dependent assay of Estrone-3-sulfate (E3S) (prototypical substrate for OAT3) uptake in HEK293 cells overexpressing OAT3 or pCMV vector following various incubation times (i.e., 1, 2, 5, 10 and 15 min.) with E3S at a concentration of 1 µM.
Figure 14B:
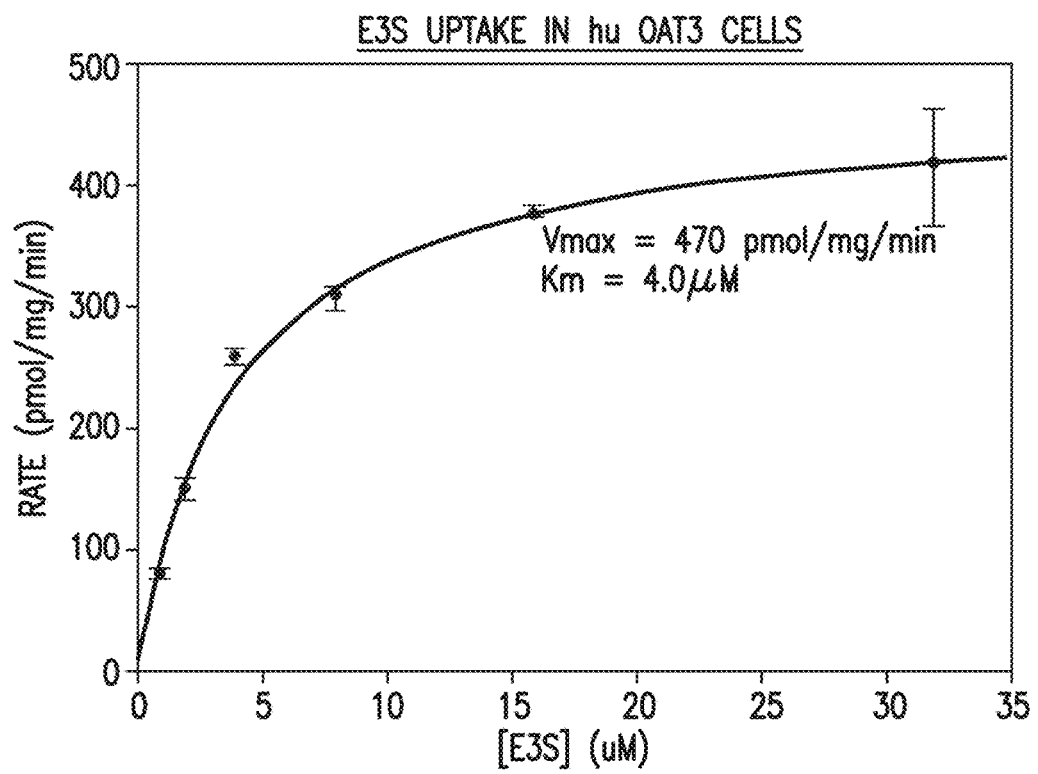
FIG. 14B is a graph depicting results of a kinetic assay whereby uptake of E3S at a concentration in the range of 0.5 to 32 µM was measured in HEK293 cells overexpressing OAT3 following incubation for 1 min. Km and Vmax, calculated using Sigma-plot, are shown as insert in the graph.
Figure 14C:
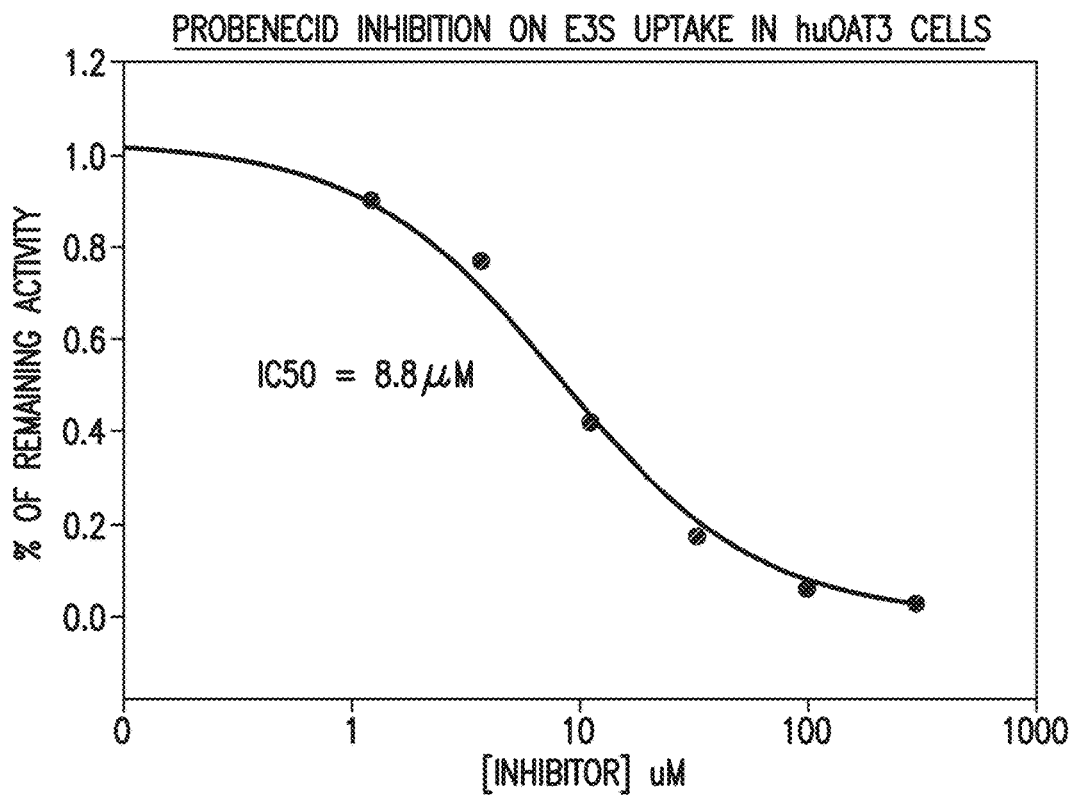
FIG. 14C is a graph depicting results of an inhibition assay whereby HEK293 cells overexpressing OAT3 were incubated with E3S at a concentration of 4 µM and probenecid (OAT3 inhibitor) at a concentration in the range of 0-300 µM for 5 min. IC50, calculated using Sigma-plot, is shown as insert in the graph.
Figure 15A:
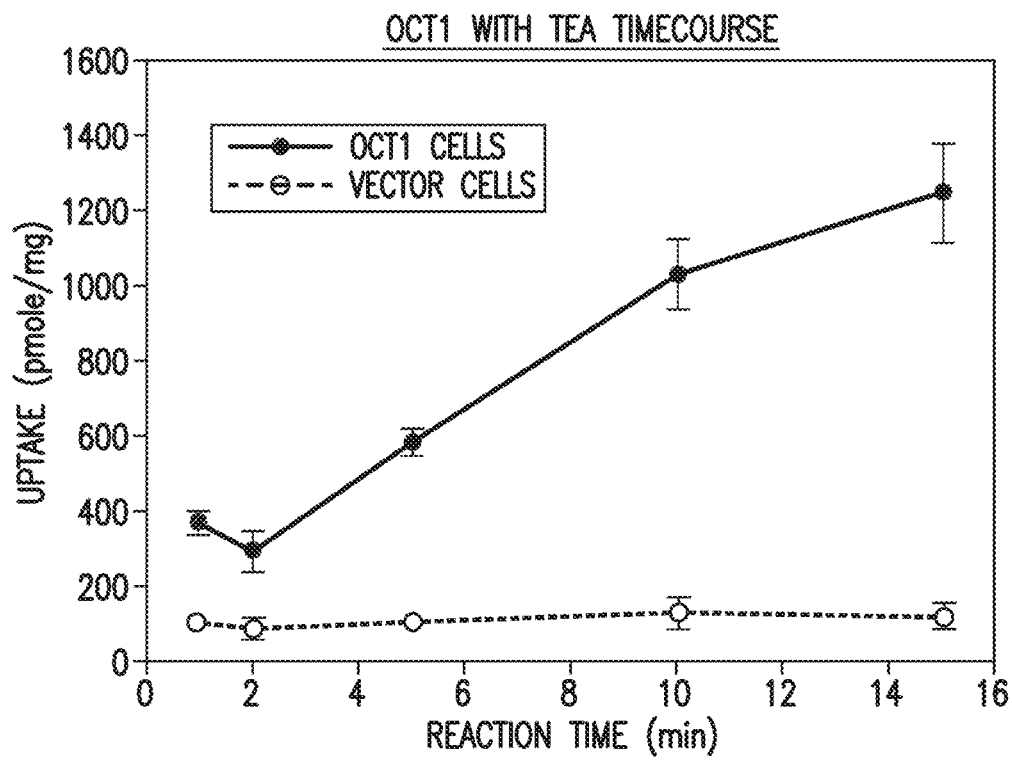
FIG. 15A is a graph depicting results of a time-dependent assay of TEA (prototypical substrate for OCT1) uptake in HEK293 cells overexpressing OCT1 or pCMV vector following various incubation times (i.e., 1, 2, 5, 10 and 15 min.) with TEA at a concentration of 31 µM.
Figure 15B:
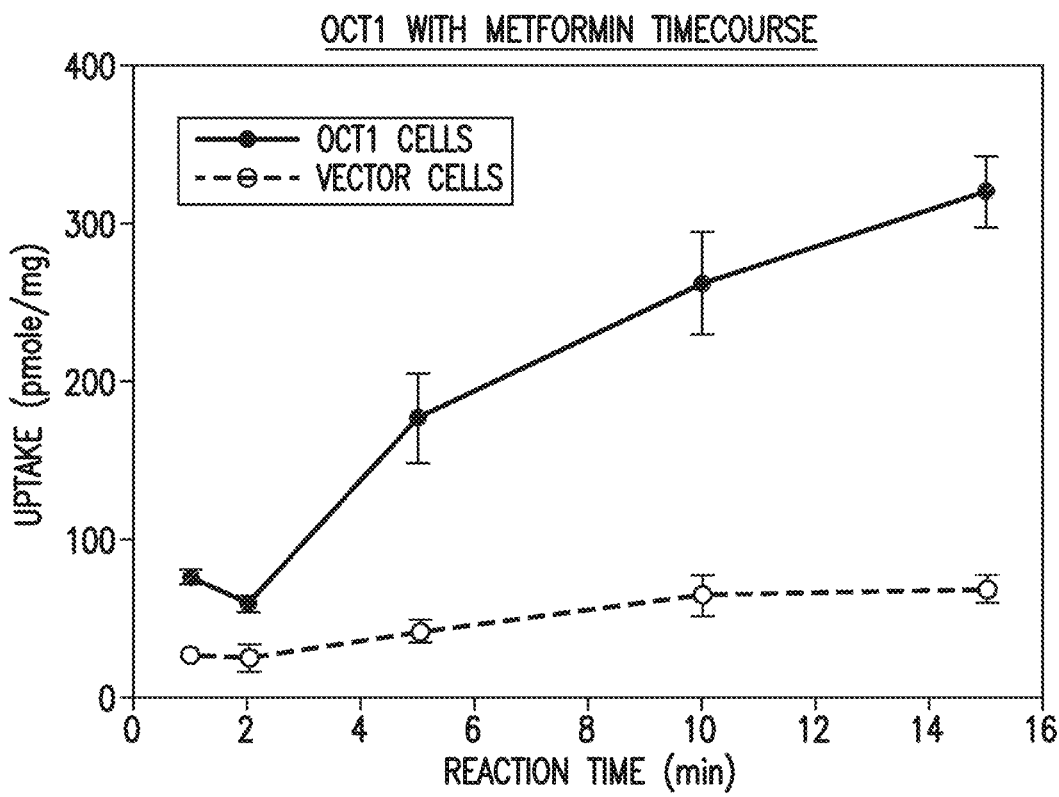
FIG. 15B is a graph depicting results of a time-dependent assay of metformin (prototypical substrate for OCT1) uptake in HEK293 cells overexpressing OCT1 or pCMV vector following various incubation times (i.e., 1, 2, 5, 10 and 15 min.) with metformin at a concentration of 3.8 µM.
Figure 15C:
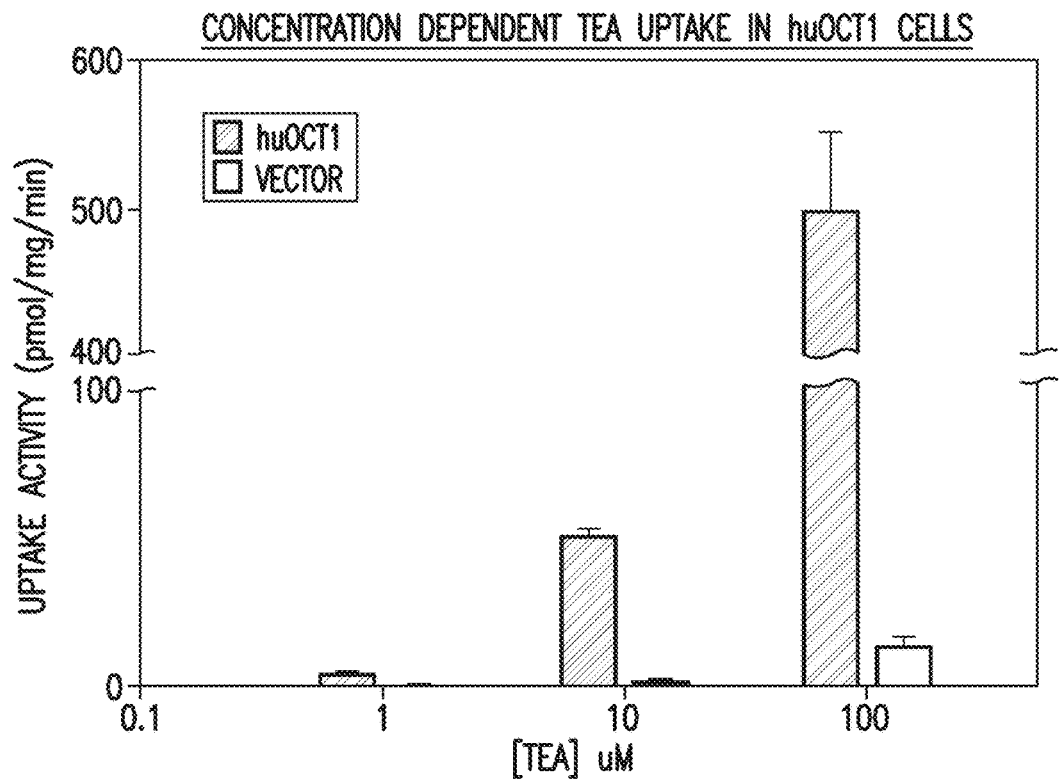
FIG. 15C is a graph depicting results of a concentration-dependent assay whereby uptake of TEA at a concentration of 1, 10 and 100 µM was measured in HEK293 cells overexpressing OCT1 or pCMV vector following incubation for 10 min.
Figure 15D:
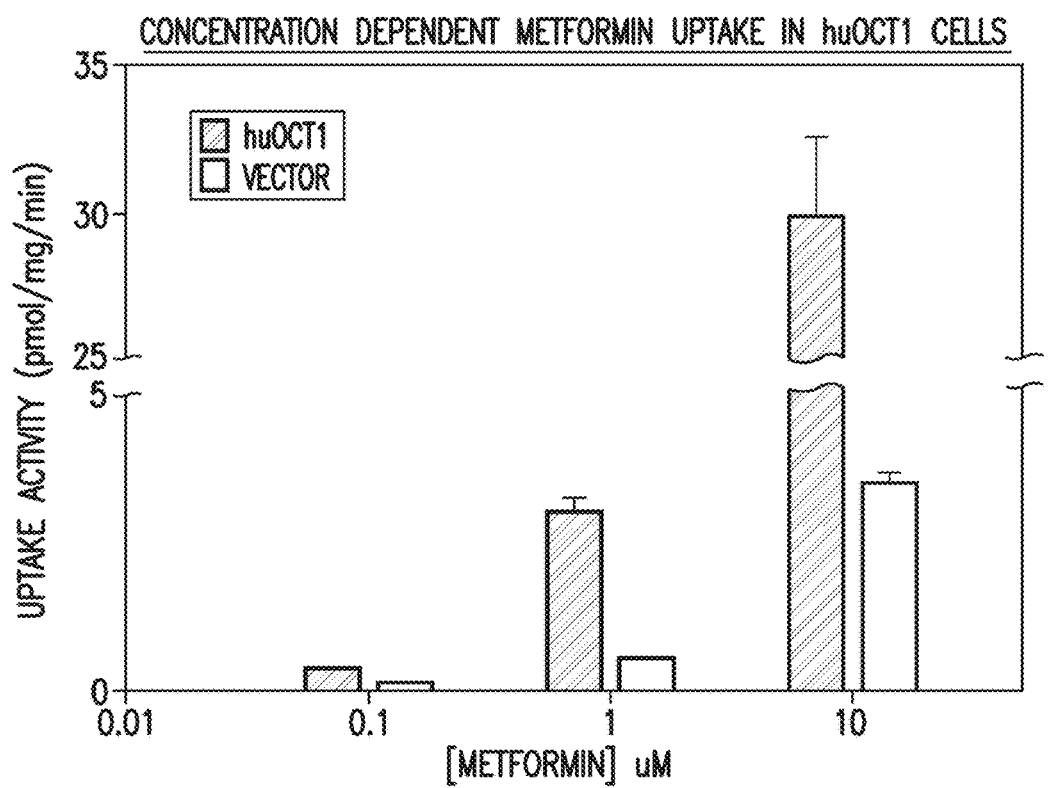
FIG. 15D is a graph depicting results of a concentration-dependent assay whereby uptake of metformin at a concentration of 0.1, 1 and 10 µM was measured in HEK293 cells overexpressing OCT1 or pCMV vector following incubation for 10 min.
Figure 15F:
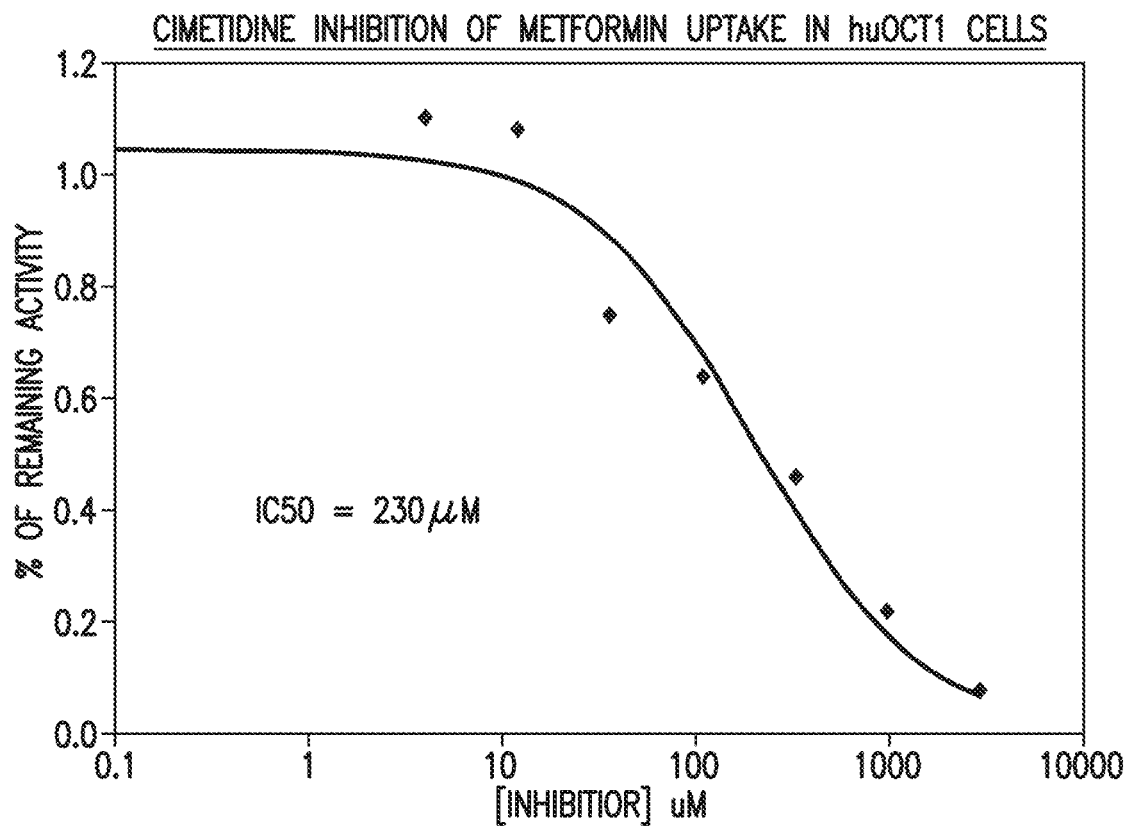
FIG. 15F is a graph depicting results of an inhibition assay whereby HEK293 cells overexpressing OCT1 were incubated with metformin at a concentration of 3.8 µM and OCT1 inhibitor cimetidine at various concentrations in the range of 4 µM to 3 mM for 10 min.
Figure 16A:
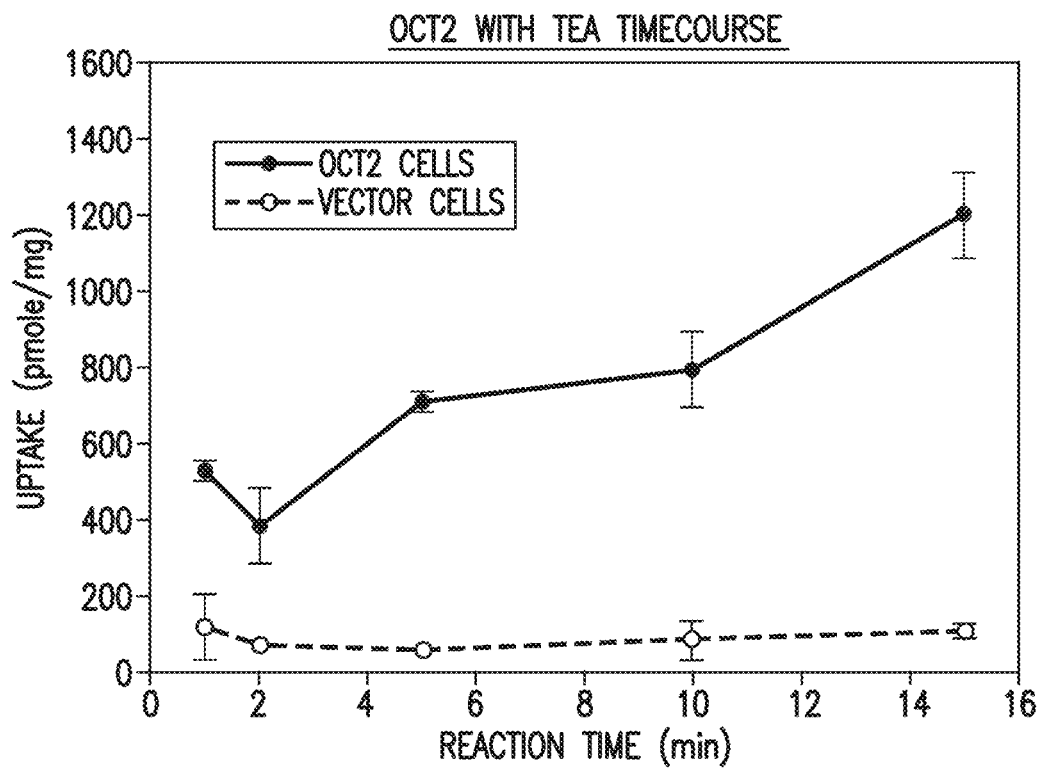
FIG. 16A is a graph depicting results of a time-dependent assay of TEA (prototypical substrate for OCT2) uptake in HEK293 cells overexpressing OCT2 or pCMV vector following various incubation times (i.e., 1, 2, 5, 10 and 15 min.) with TEA at a concentration of 31 µM.
Figure 16B:
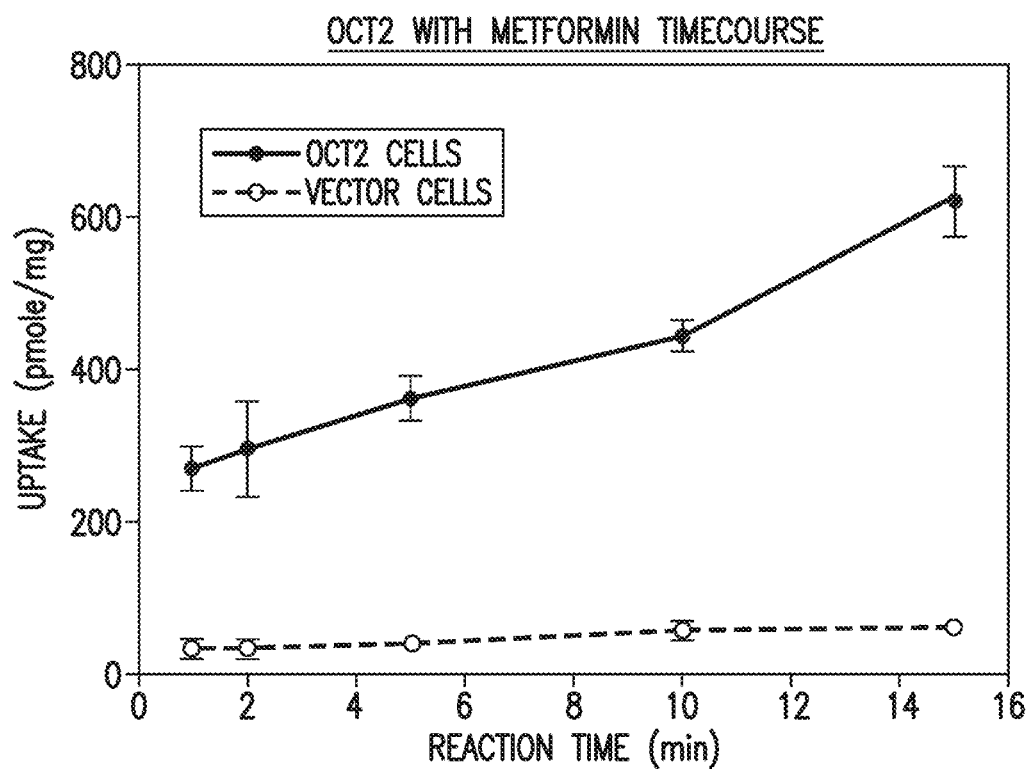
FIG. 16B is a graph depicting results of a time-dependent assay of metformin (prototypical substrate for OCT2) uptake in HEK293 cells overexpressing OCT2 or pCMV vector following various incubation times (i.e., 1, 2, 5, 10 and 15 min.) with metformin at a concentration of 3.8 µM.
Figure 16C:
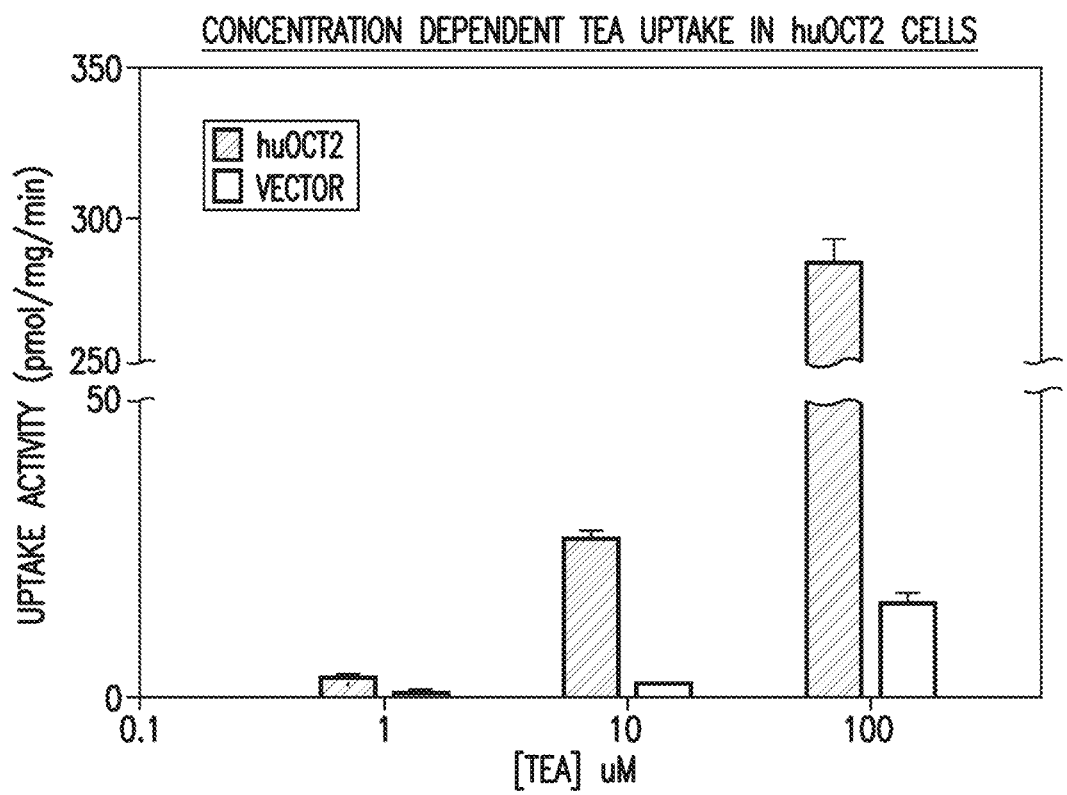
FIG. 16C is a graph depicting results of a concentration-dependent assay whereby uptake of TEA at a concentration of 1, 10 and 100 µM was measured in HEK293 cells overexpressing OCT2 or pCMV vector following incubation for 10 min.
Figure 16D:
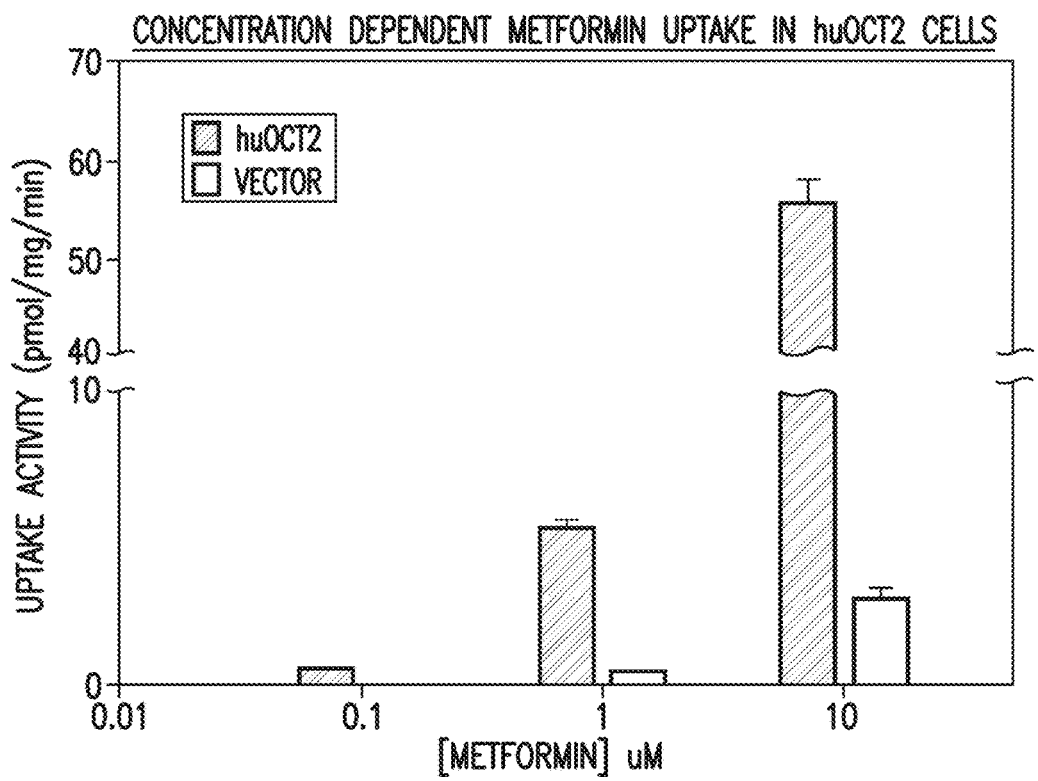
FIG. 16D is a graph depicting results of a concentration-dependent assay whereby uptake of metformin at a concentration of 0.1, 1 and 10 µM was measured in HEK293 cells overexpressing OCT2 or pCMV vector following incubation for 10 min.
Figure 16E:
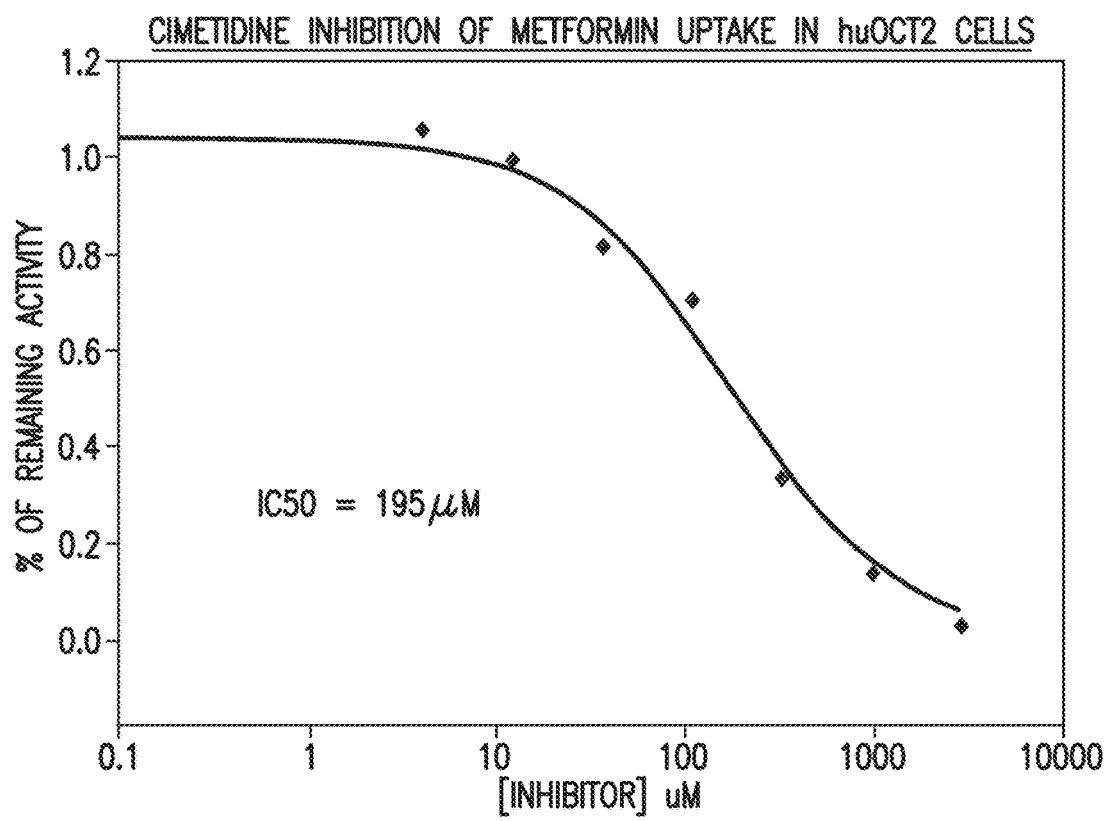
FIG. 16E is a graph depicting results of an inhibition assay whereby HEK293 cells overexpressing OCT2 were incubated with metformin at a concentration of 3.8 µM and OCT2 inhibitor cimetidine at a concentration in the range of 4 µM to 3 mM for 10 min. IC50, calculated using Sigma-plot, is shown as insert in the graph.
Figure 17A:
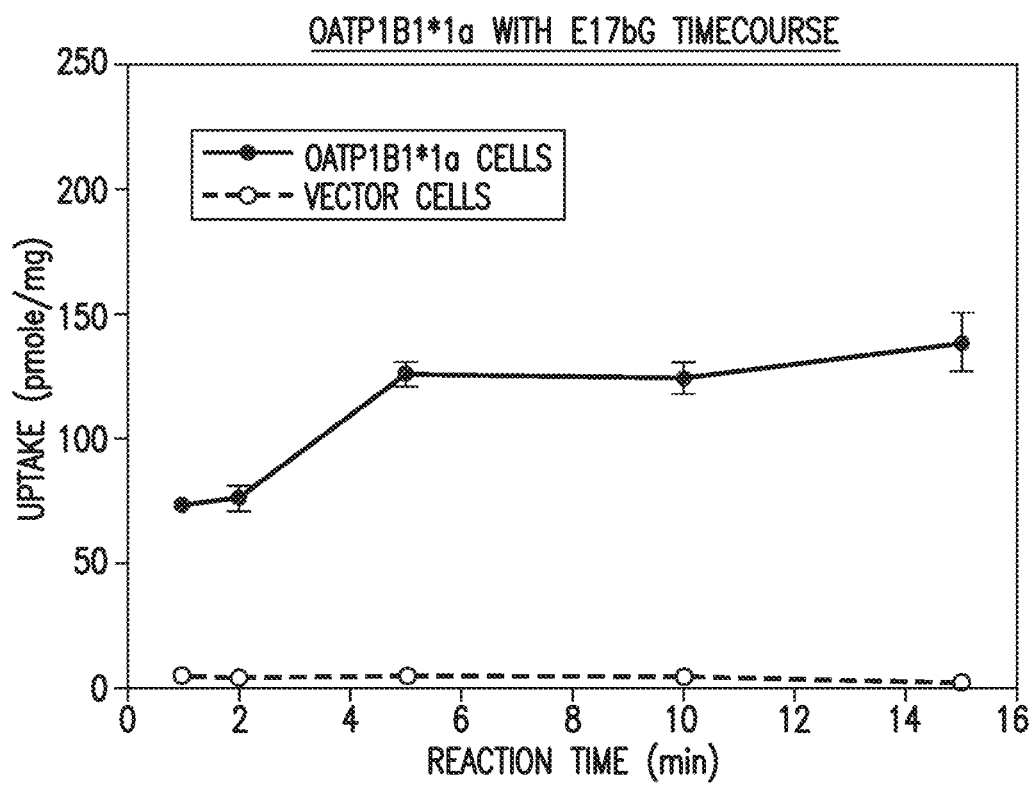
FIG. 17A is a graph depicting results of a time-dependent assay of estradiol-17β-glucuronide (E17βG) uptake in HEK293 cells overexpressing OATP1B1*1a or pCMV vector following various incubation times (i.e., 1, 2, 5, 10 and 15 min.) with E17βG at a concentration of 1 µM.
Figure 17B:
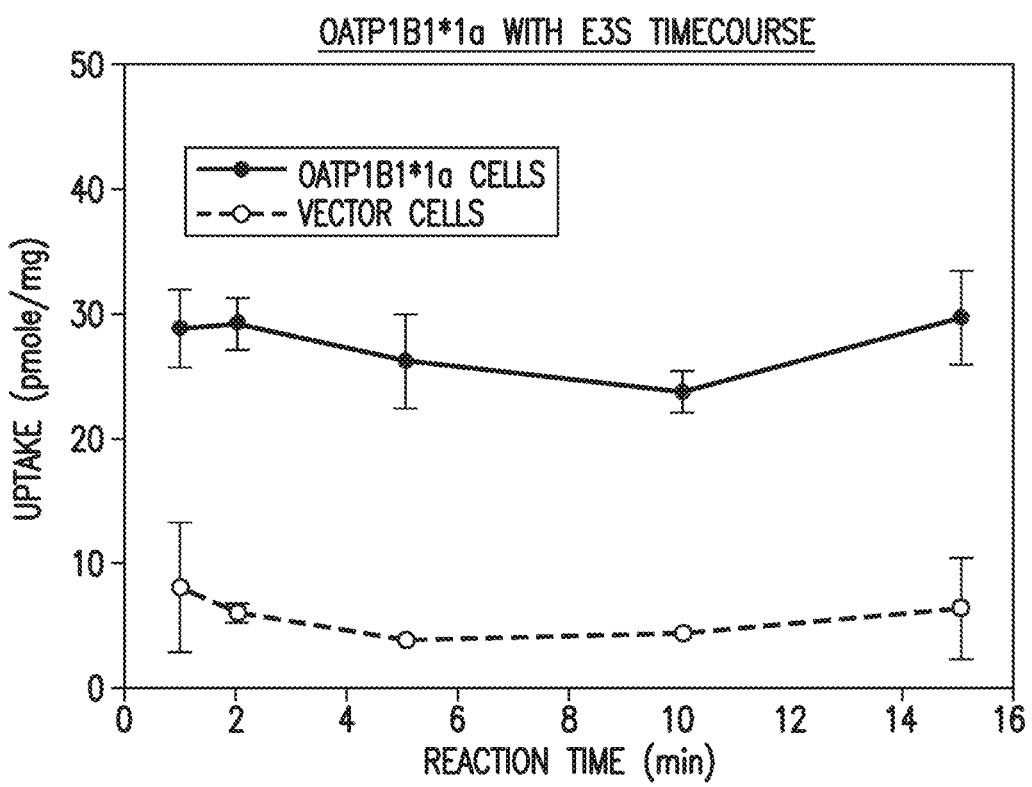
FIG. 17B is a graph depicting results of a time-dependent assay of estrone-3-sulfate (E3S) uptake in HEK293 cells overexpressing OATP1B1*1a or pCMV vector following various incubation times (i.e., 1, 2, 5, 10 and 15 min.) with E3S at a concentration of 1 µM.
Figure 17C:
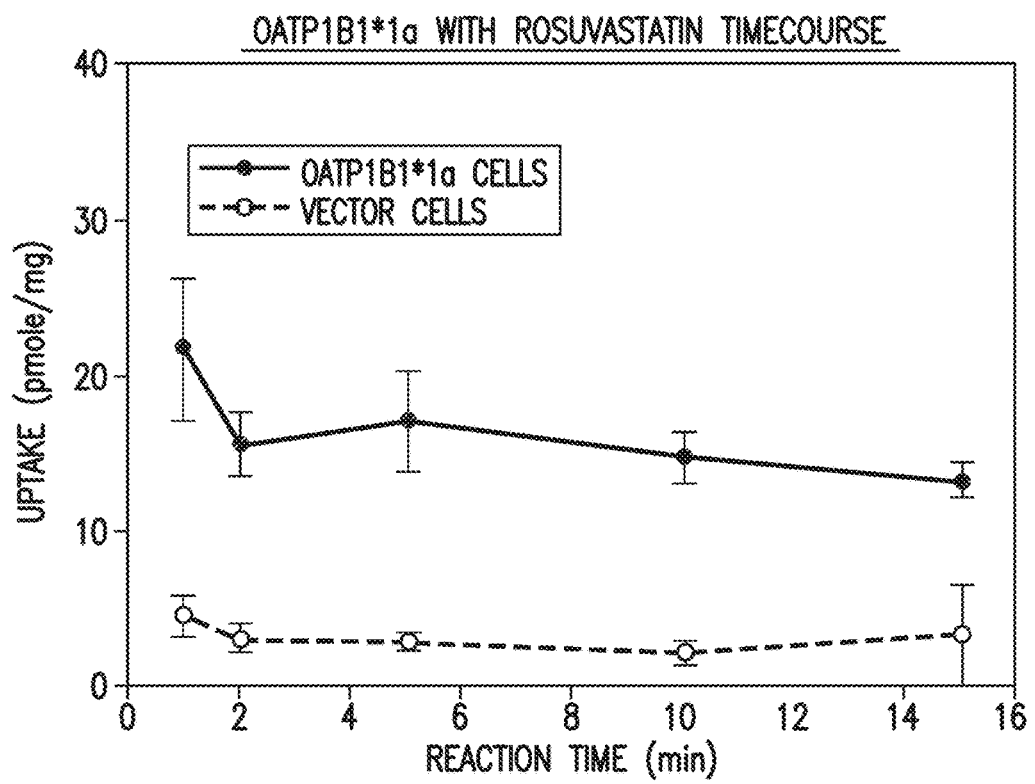
FIG. 17C is a graph depicting results of a time-dependent assay of rosuvastatin uptake in HEK293 cells overexpressing OATP1B1*1a or pCMV vector following various incubation times (i.e., 1, 2, 5, 10 and 15 min.) with rosuvastatin at a concentration of 1 µM.
Figure 17D:
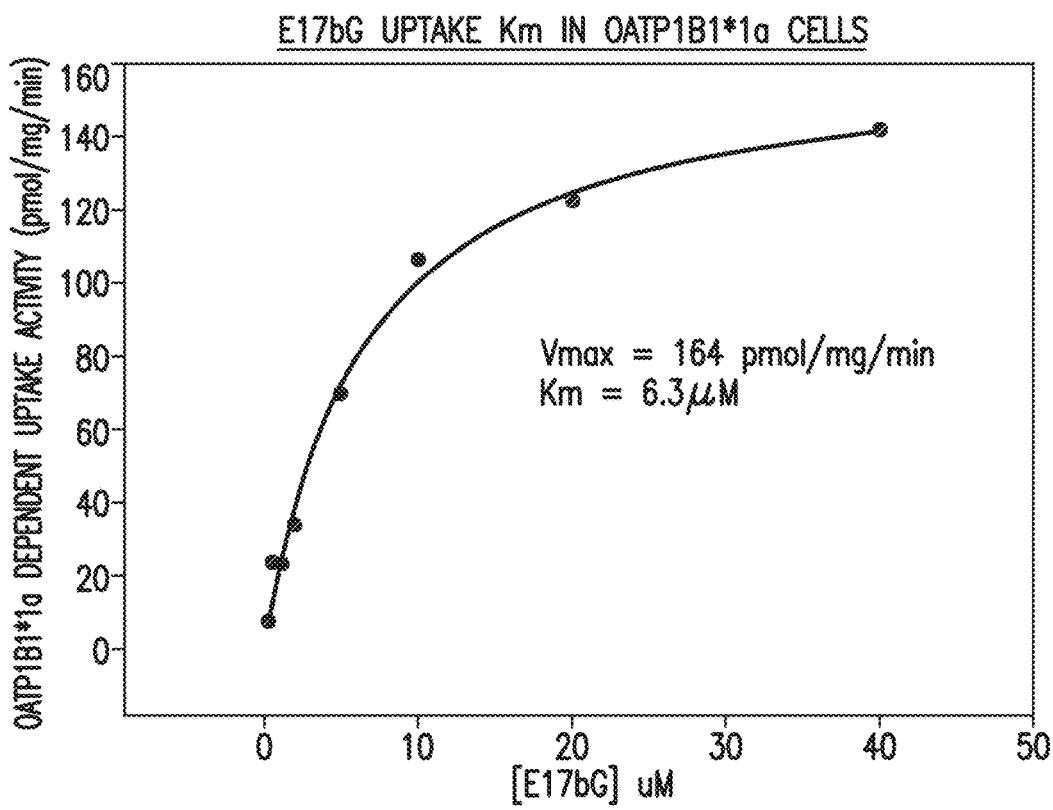
FIG. 17D is a graph depicting results of a concentration-dependent assay whereby uptake of E17βG at a concentration in the range of 0.25 to 40 µM was measured in HEK293 cells overexpressing OATP1B1*1a following incubation for 1 min Km and Vmax, calculated using Sigma-plot, are shown as insert in the graph.
Figure 17E:
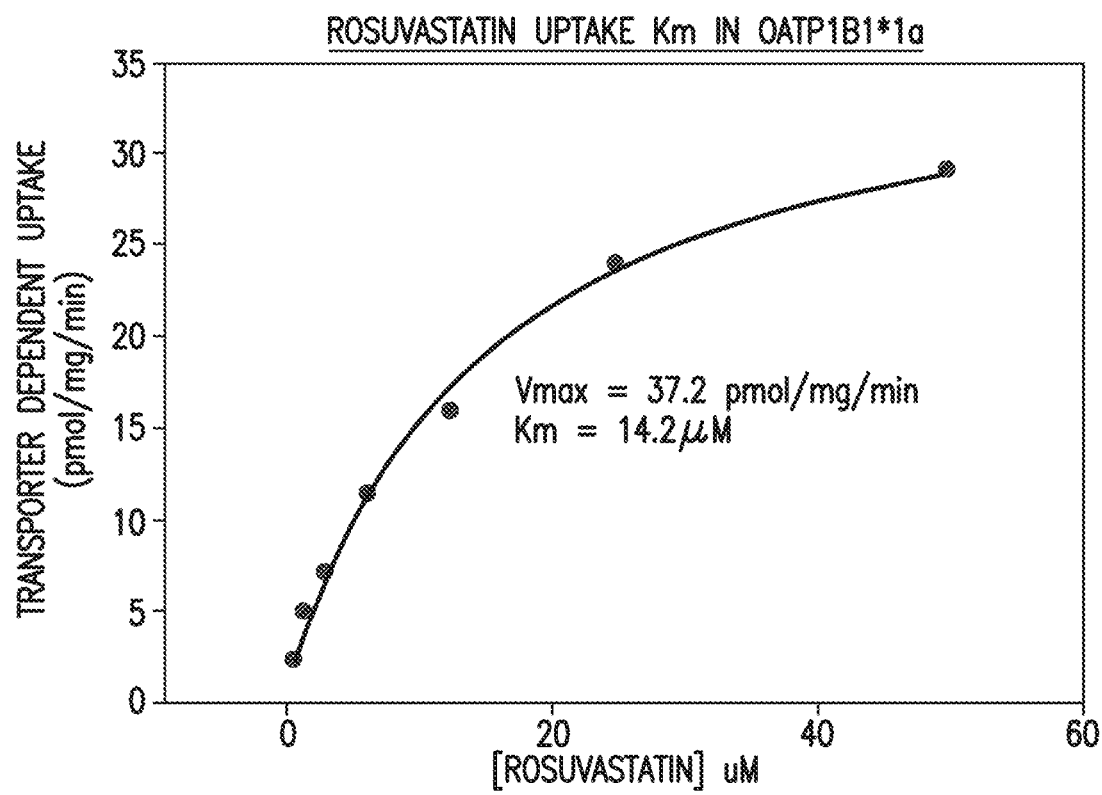
FIG. 17E is a graph depicting results of a concentration-dependent assay whereby uptake of rosuvastatin at a concentration in the range of 0.78 to 50 µM was measured in HEK293 cells overexpressing OATP1B1*1a following incubation for 5 min. Km and Vmax, calculated using Sigma-plot, are shown as insert in the graph.
Figure 17F:
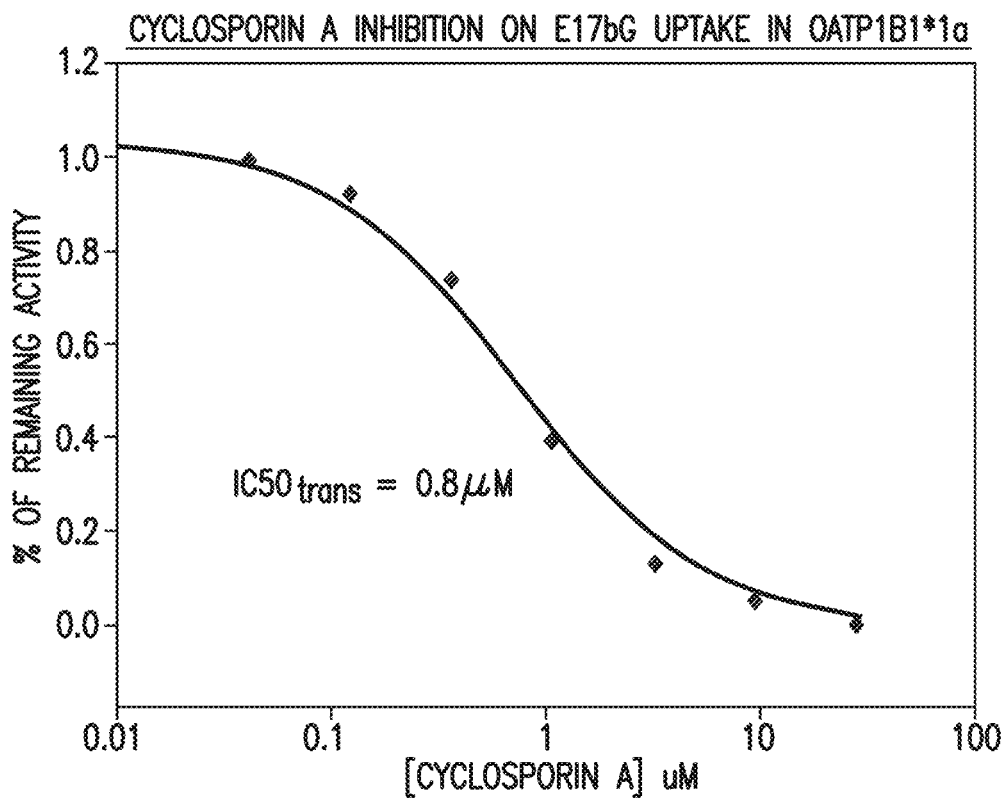
FIG. 17F is a graph depicting results of an inhibition assay whereby uptake of E17βG at a concentration of 1 µM was measured in HEK293 cells overexpressing OATP1B1*1a following incubation with inhibitor cyclosporin A at a concentration in the range of 0.04 to 30 µM for 5 min. IC50, calculated using Sigma-plot, is shown as insert in the graph.
Figure 18A:
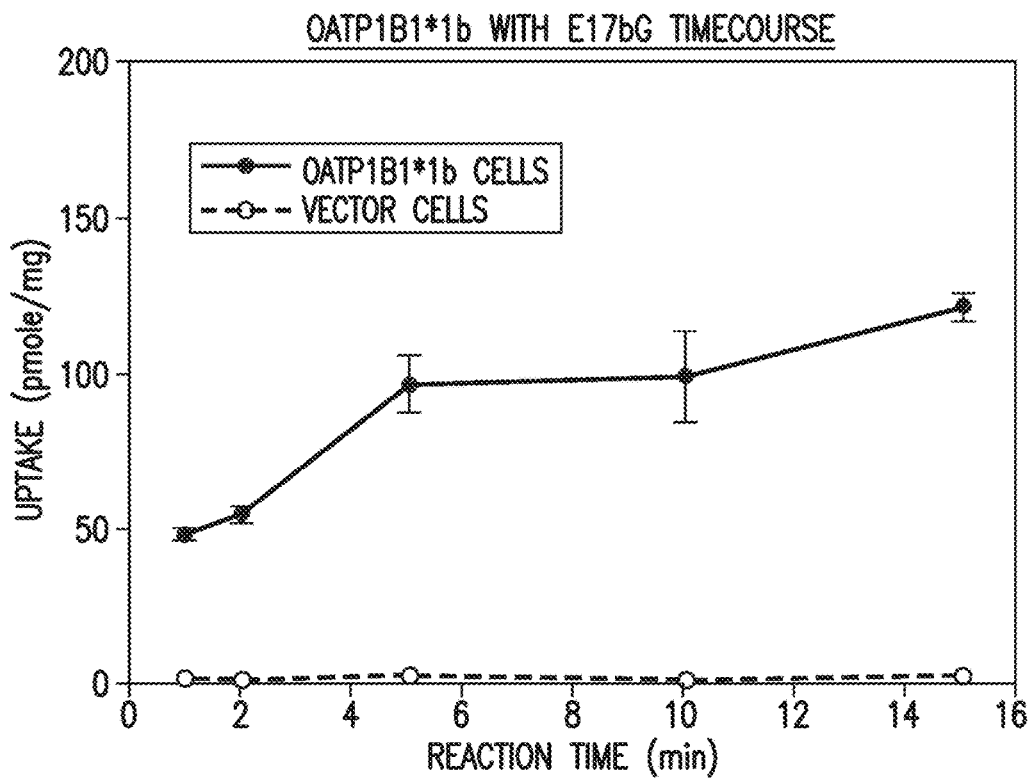
FIG. 18A is a graph depicting results of a time-dependent assay of E17βG uptake in HEK293 cells overexpressing OATP1B1*1b or pCMV vector following various incubation times (i.e., 1, concentration of 1 µM.2, 5, 10 and 15 min.) with E17βG at a concentration of 1 µM.
Figure 18B:
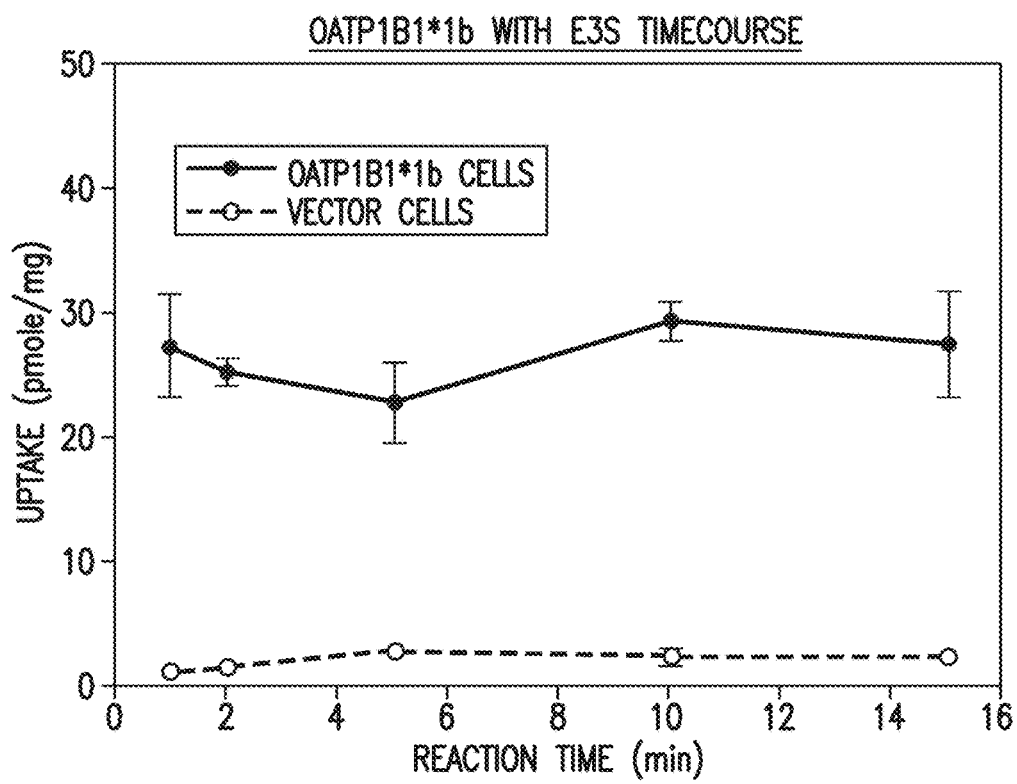
FIG. 18B is a graph depicting results of a time-dependent assay of E3S uptake in HEK293 cells overexpressing OATP1B1*1b or pCMV vector following various incubation times (i.e., 1, 2, 5, 10 and 15 min.) with E3S at a concentration of 1 µM.
Figure 18C:
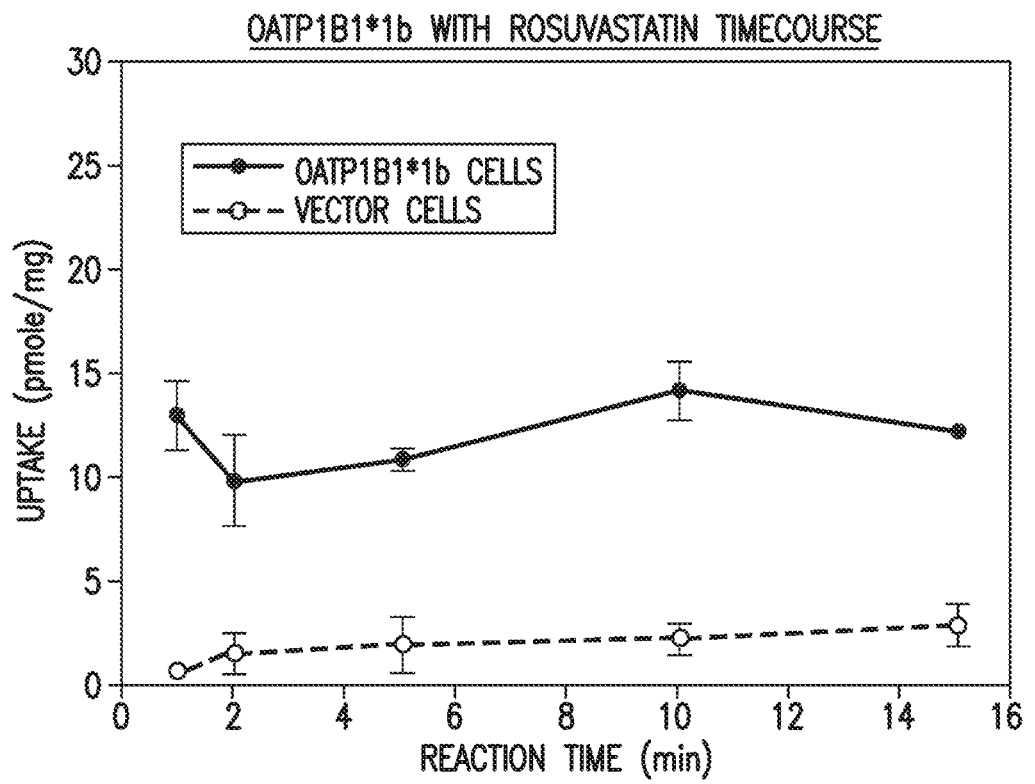
FIG. 18C is a graph depicting results of a time-dependent assay of rosuvastatin uptake in HEK293 cells overexpressing OATP1B1*1b or pCMV vector following various incubation times (i.e., 1, 2, 5, 10 and 15 min.) with rosuvastatin at a concentration of 1 µM.
Figure 18D:
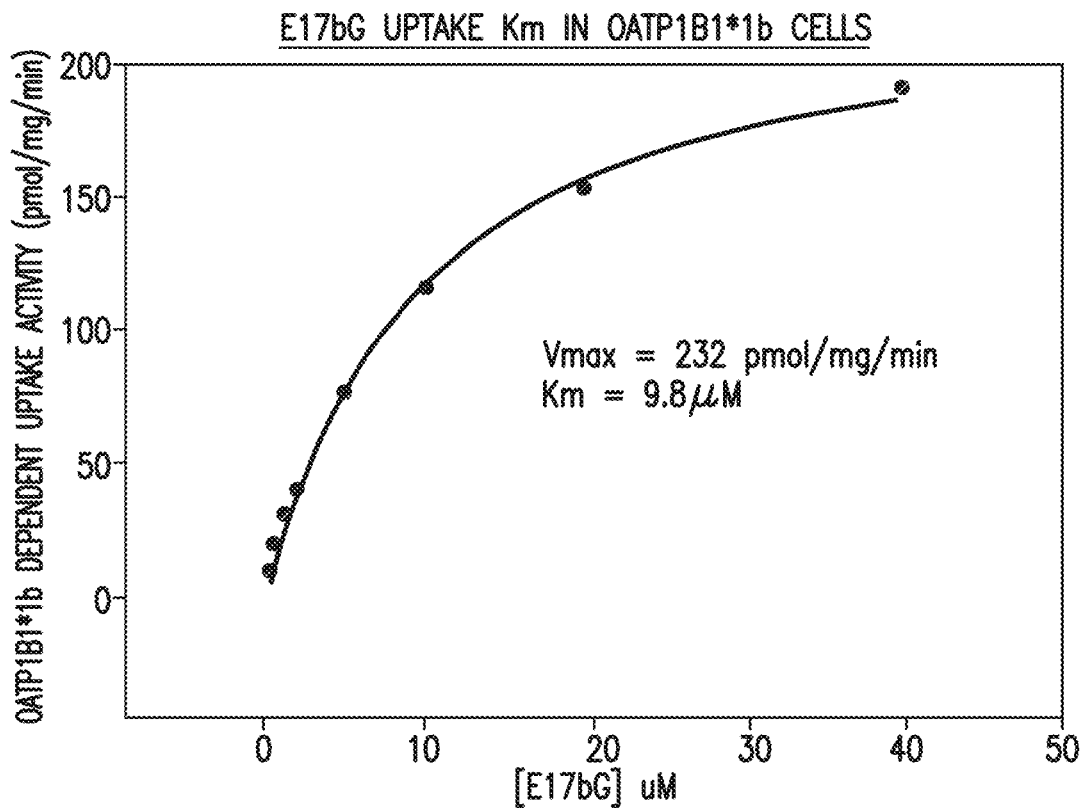
FIG. 18D is a graph depicting results of a concentration-dependent assay whereby uptake of E17βG at a concentration in the range of 0.25 to 40 µM was measured in HEK293 cells overexpressing OATP1B1*1b following incubation for 1 min. Km and Vmax, calculated using Sigma-plot, are shown as insert in the graph.
Figure 18E:
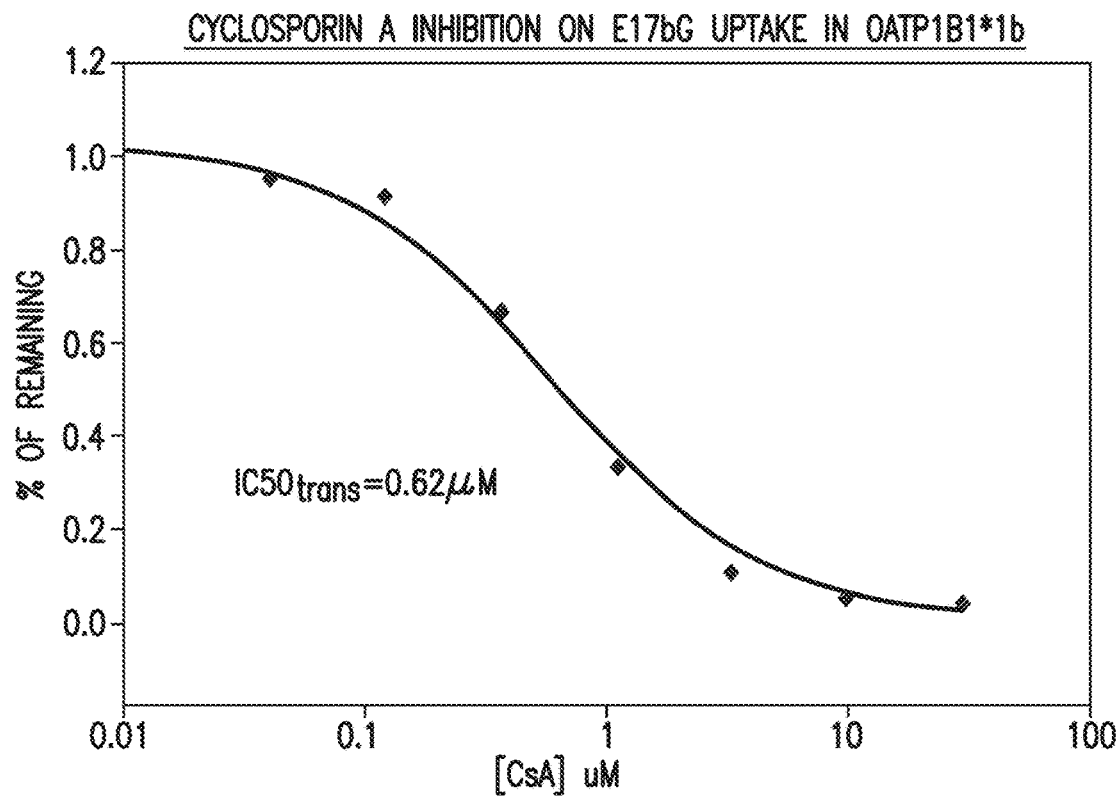
FIG. 18E is a graph depicting results of an inhibition assay whereby uptake of E17βG at a concentration of 1 µM was measured in HEK293 cells overexpressing OATP1B1*1b following incubation with inhibitor cyclosporin A at a concentration in the range of 0.04 to 30 µM for 5 min IC50, calculated using Sigma-plot, is shown as insert in the graph.
Figure 19A:
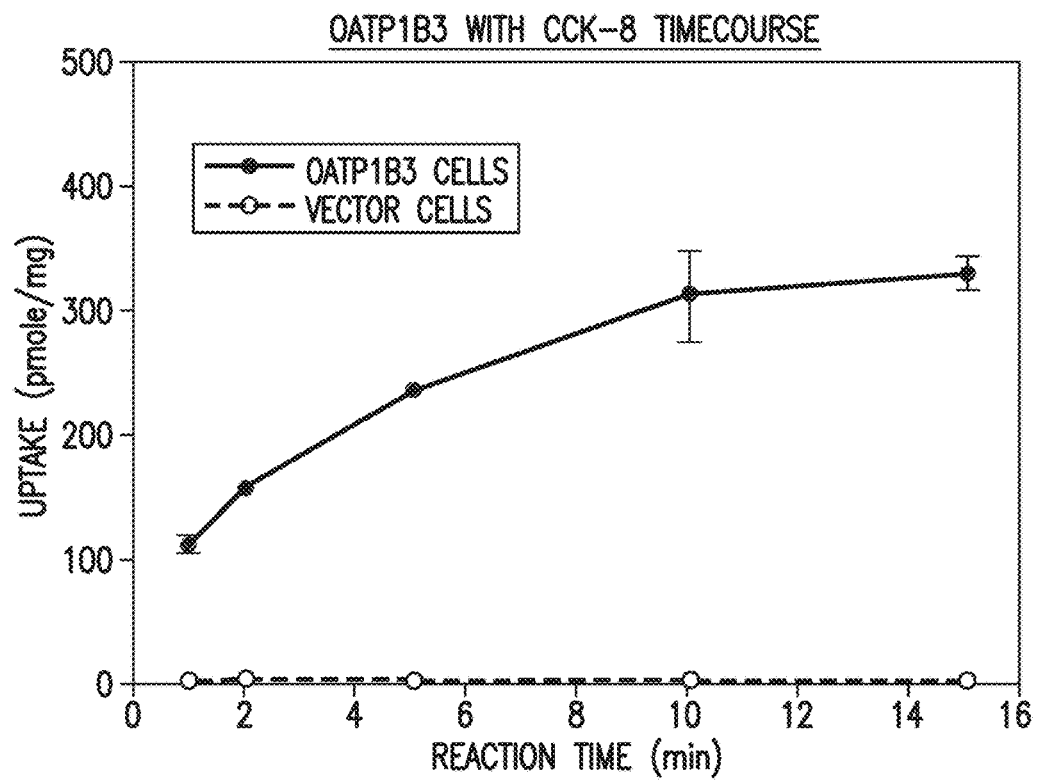
FIG. 19A is a graph depicting results of a time-dependent assay of cholecystokinin (CCK-8) uptake in HEK293 cells overexpressing OATP1B3 or pCMV vector following various incubation times (i.e., 1, 2, 5, 10 and 15 min.) with CCK-8 at a concentration of 1 µM.
Figure 19B:
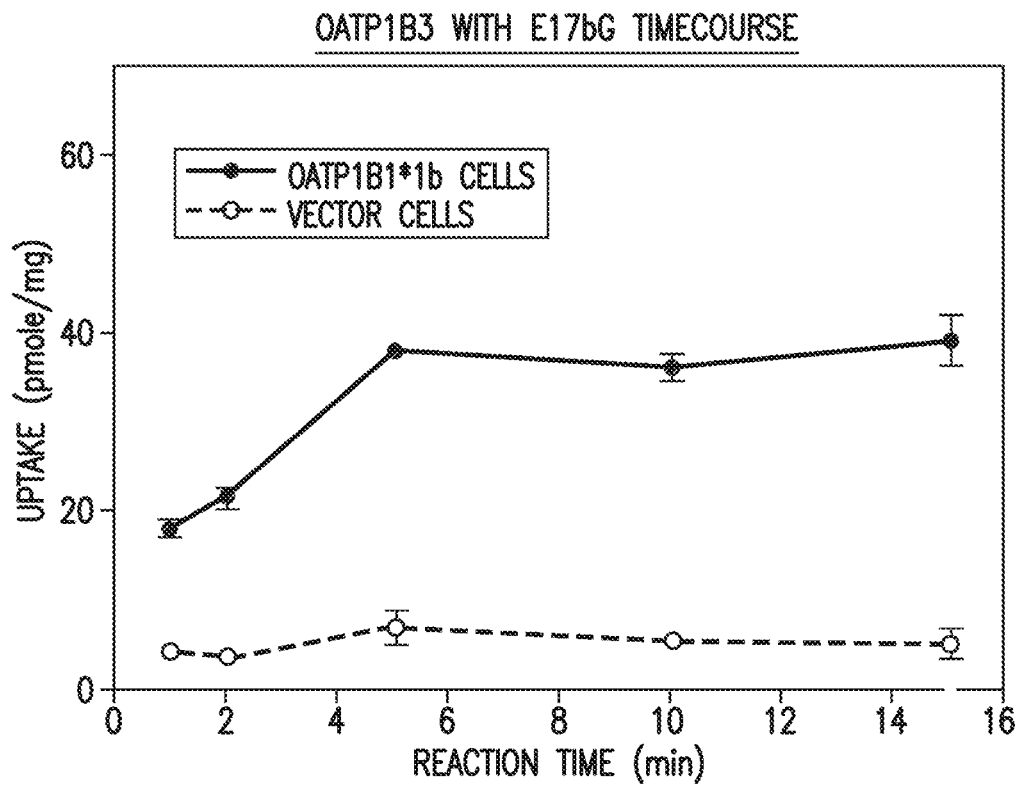
FIG. 19B is a graph depicting results of a time-dependent assay of E17βG uptake in HEK293 cells overexpressing OATP1B3 or pCMV vector following various incubation times (i.e., 1, 2, 5, 10 and 15 min.) with E17βG at a concentration of 1 µM.
Figure 19C:
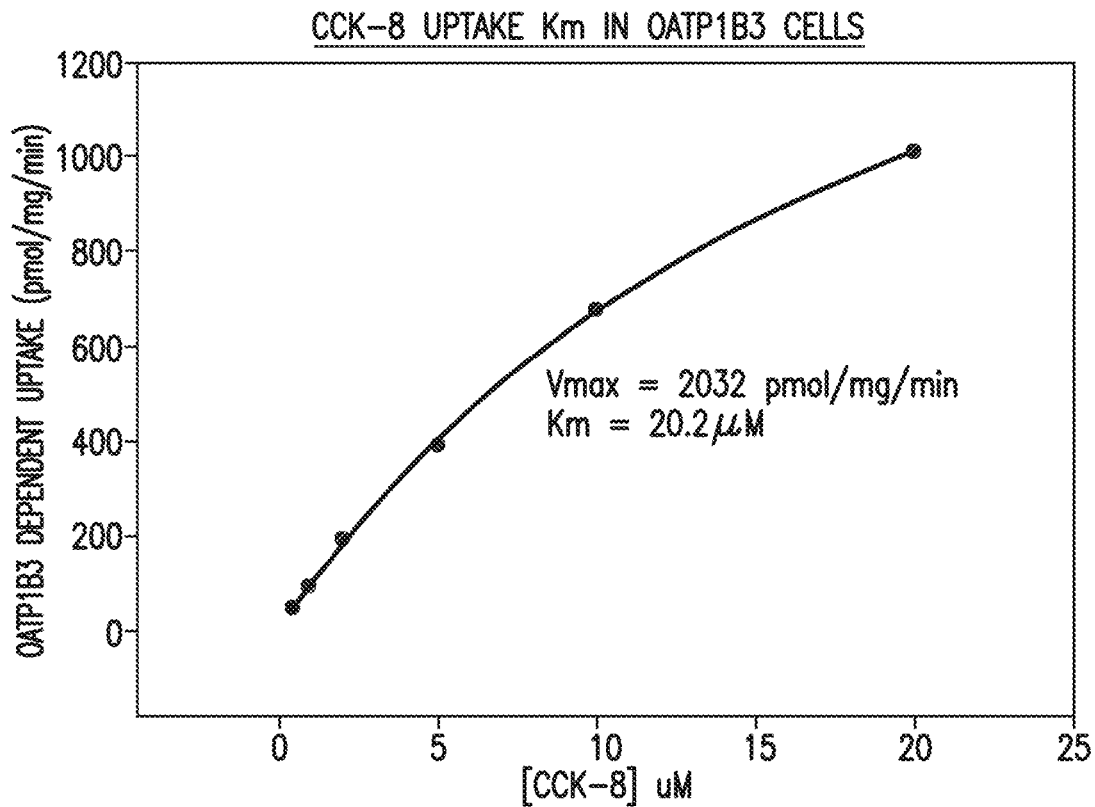
FIG. 19C is a graph depicting results of a concentration-dependent assay whereby uptake of CCK-8 at a concentration in the range of 0.5 to 20 µM was measured in HEK293 cells overexpressing OATP1B3 following incubation for 1 min. Km and Vmax, calculated using Sigma-plot, are shown as insert in the graph.
Figure 19D:
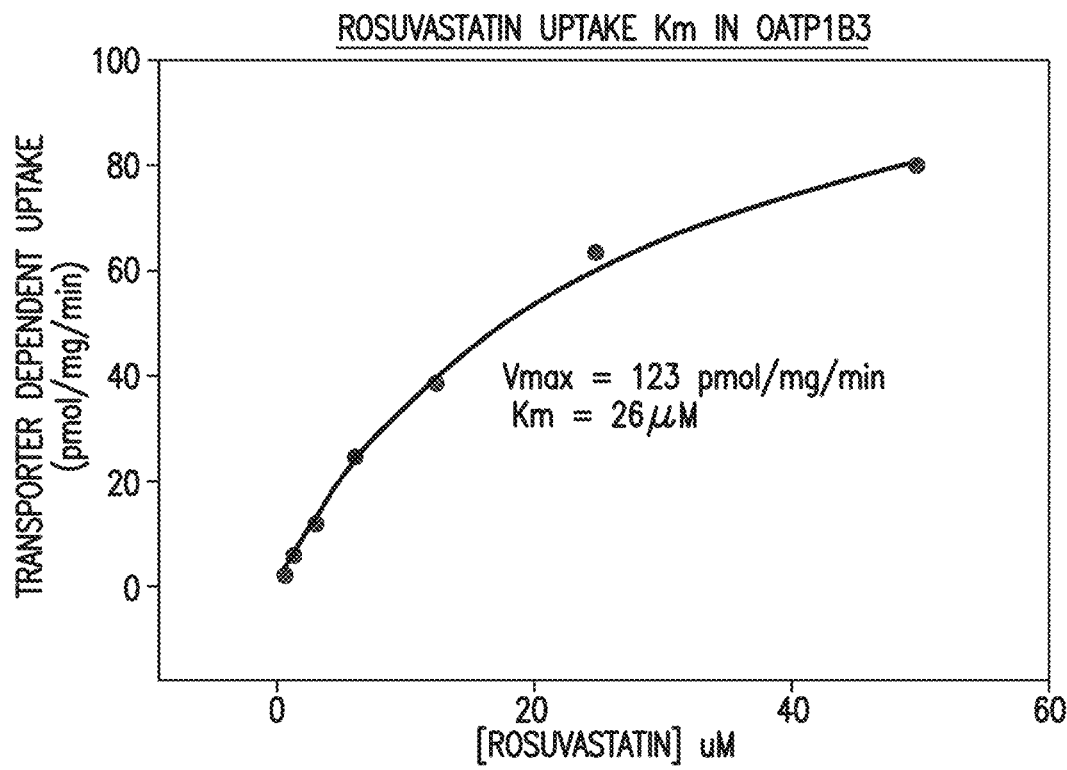
FIG. 19D is a graph depicting results of a concentration-dependent assay whereby uptake of rosuvastatin at a concentration in the range of 0.78 to 50 µM was measured in HEK293 cells overexpressing OATP1B3 following incubation for 5 min. Km and Vmax, calculated using Sigma-plot, are shown as insert in the graph.
Figure 19E:
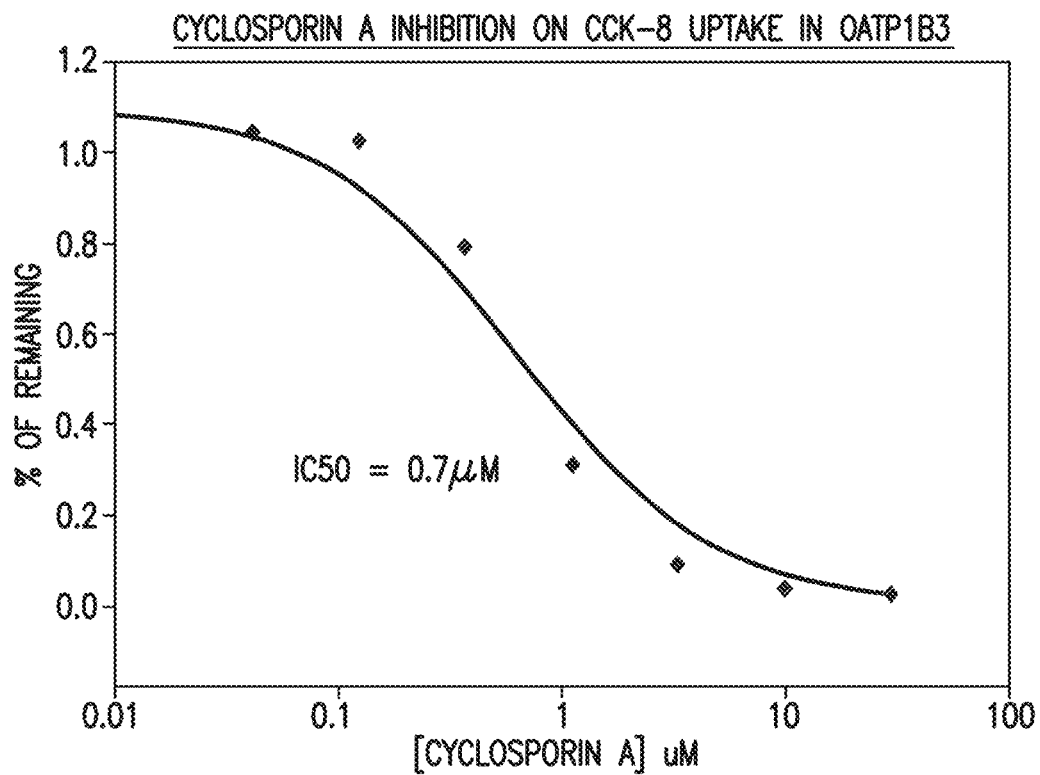
FIG. 19E is a graph depicting results of an inhibition assay whereby uptake of CCK-8 at a concentration of 1 µM was measured in HEK293 cells overexpressing OATP1B3 following incubation with inhibitor cyclosporin A at a concentration in the range of 0.04 to 30 µM for 2 min. IC50, calculated using Sigma-plot, is shown as insert in the graph.

As illustrated in FIG. 12, each of the 8 cryopreserved recombinant cells formed a confluent monolayer following thawing, plating on Poly-D-Lysine plates and incubation for 24-hrs post-plating.

As illustrated in FIGS. 13-19 and Tables 13-14, the kinetic and inhibition profiles examined in cryopreserved recombinant cells expressing a transporter protein was consistent with reported values. Specifically, as illustrated in FIGS. 13A-13C, the kinetics of PAH uptake by recombinant cells expressing OAT1 and inhibition profile of probenecid thereof is consistent with reported values. As illustrated in FIGS. 14A-14C, the kinetics of E3S uptake by recombinant cells expressing OAT3 and inhibition profile of probenecid thereof is consistent with reported values. As illustrated in FIGS. 15A-15F, the kinetics of TEA and metformin uptake by recombinant cells expressing OCT1 as well as inhibition profile thereof is consistent with reported values. As illustrated in FIGS. 16A-16E, the kinetics of TEA and metformin uptake by recombinant cells expressing OCT2 as well as inhibition profile is consistent with reported values. As illustrated in FIGS. 17A-17F, the kinetics of E17βG, E3S and rosuvastatin uptake by recombinant cells expressing OATP1B1*1a as well as inhibition profile of E17βG uptake by cyclosporin A is consistent with reported values. As illustrated in FIGS. 18A-18E, the kinetics of E17βG, E3S and rosuvastatin uptake by recombinant cells expressing OATP1B1*1b as well as inhibition profile of E17βG uptake by cyclosporin A is consistent with reported values. As illustrated in FIGS. 19A-19E and Tables 13-14, the kinetics of CCK-8, E17βG and rosuvastatin uptake by recombinant cells expressing OATP1B3 as well as inhibition profile of CCK-8 uptake by cyclosporin A is consistent with reported values.

TABLE 13

| SLC Transporter Cells | | | | Literature Report | |
|---|---|---|---|---|---|
| Transporter | Substrate | $K_m$ (µM) | $K_m$ (µM) | Test System | Literature |
| OATP1B1*1a | E17βG | 6.2 | 6.3 | HEK293 cells | P. Sharma, et al. Xenobiotica 40:24. 2010 |
| OATP1B3 | CCK-8 | 20.2 | 16.5 | CHO Cells | Poirier A, et al., J Pharmacokinet |
| OAT1 | PAH | 87.3 | 28 | HEK293 cells | Ueo H, et al., Biochem Pharmacol., 2005 |
| OAT3 | E3S | 4.0 | 6.3 | HEK293 cells | Ueo H, et al., Biochem Pharmacol., 2005 |

TABLE 14

| Corning® SLC TransportoCells™ | | | | Literature Report | |
|---|---|---|---|---|---|
| Transporter | Substrate | Inhibitor | IC50 (µM) | IC50 (µM) | Test System | Literature |
| OATP1B1*1a | E17βG | Cyclosporin A | 0.8 | 0.7 | HEK293 Cells | MG Soars, et al., Drug Metab |
| OATP1B3 | CCK-8 | Cyclosporin A | 0.7 | 0.6 | HEK293 Cells | Bednarczyk D. Anal Biochem. |
| OAT1 | PAH | Probenecid | 7.2 | 6.5 | CHO | Ho ES, et al., J Am Soc |
| OAT3 | E3S | Probenecid | 8.8 | 9 | S2 | Takeda M, et al., Eur J Pharmacol., |
| OCT1 | Metformin | Cimetidine | 230 | 104 | HEK293 Cells | Sumito I, et al., JPET, 2011 |
| OCT2 | Metformin | Cimetidine | 195 | 124 | HEK293 Cells | Sumito I, et al., JPET, 2011 |

It will be appreciated by those skilled in the art that changes could be made to the embodiments described above without departing from the broad inventive concept thereof. It is understood, therefore, that this invention is not limited to the particular embodiments disclosed, but is intended to cover modifications that are within the spirit and scope of the invention, as defined by the appended claims.

What is claimed is:

1. A cryopreserved recombinant cell comprising one or more transiently overexpressed genes encoding a drug transporter protein, wherein activity of the drug transporter protein is detectable in a population of the cryopreserved recombinant cells following thaw from cryopreservation, wherein the cryopreserved recombinant cell is transiently transfected with the one or more genes by a method comprising electroporation, and wherein said one or more genes is MATE1 and wherein said cell is HEK293.

2. The recombinant cell of claim 1, wherein said one or more genes is derived individually from human or an animal species selected from mouse, rat, guinea pigs, dog, and monkey.

3. The recombinant cell of claim 1, wherein activity of the drug transporter protein is detectable in a population of said cell at least 24 hours post plating following thaw from cryopreservation.

4. The recombinant cell of claim 1, wherein activity of the drug transporter protein is detectable in a population of said cell at least 48 hours post plating following thaw from cryopreservation.

5. The recombinant cell of claim 1, wherein activity of the drug transporter protein is detectable in a population of said cell at least 72 hours post plating following thaw from cryopreservation.

6. A process of preparing cryopreserved transiently transfected recombinant cells, the process comprising:
transiently transfecting cells with one or more genes encoding a drug transporter protein to provide the transiently transfected recombinant cells; and
cryopreserving the transiently transfected recombinant cells within 48 hours of transfection, wherein the transient transfection of the cells comprises electroporation; wherein said one or more genes is MATE1 and wherein said cell is HEK293.

7. The process of claim 6, wherein the transiently transfected recombinant cells are cryopreserved at 30 minutes to 24 hours post transfection.

8. A cryopreserved transiently transfected recombinant cell prepared according to the process of claim 6.

* * * * *

UNITED STATES PATENT AND TRADEMARK OFFICE
CERTIFICATE OF CORRECTION

PATENT NO. : 10,629,064 B2
APPLICATION NO. : 16/407860
DATED : April 21, 2020
INVENTOR(S) : Na Li et al.

It is certified that error appears in the above-identified patent and that said Letters Patent is hereby corrected as shown below:

On the Title Page

On page 2, in Column 2, item (56), Other Publications, Line 38, delete ""Comparitive" and insert -- "Comparative --, therefor.

On page 2, in Column 2, item (56), Other Publications, Line 53, delete "infomahealthcare" and insert -- informahealthcare --, therefor.

On page 2, in Column 2, item (56), Other Publications, Line 55, delete "Catechol O" and insert -- Catechol-O --, therefor.

On page 2, in Column 2, item (56), Other Publications, Line 56, delete "chartacterization" and insert -- characterization --, therefor.

On page 2, in Column 2, item (56), Other Publications, Line 61, delete "Therapeutics,May" and insert -- Therapeutics, May --, therefor.

Signed and Sealed this
Fourteenth Day of July, 2020

Andrei Iancu
*Director of the United States Patent and Trademark Office*